United States Patent
Nielsen et al.

(10) Patent No.: US 12,133,936 B2
(45) Date of Patent: Nov. 5, 2024

(54) SURGICAL SYSTEM AND METHODS OF USE

(71) Applicant: MEDTRONIC INC., Minneapolis, MN (US)

(72) Inventors: Christian S. Nielsen, River Falls, WI (US); Sean Chen, Plymouth, MN (US); Anne R. Kamm, White Bear Lake, MN (US); Paul C. Ray, Maple Grove, MN (US)

(73) Assignee: Medtronic, Inc, Minneapolis, MN (US)

( * ) Notice: Subject to any disclaimer, the term of this patent is extended or adjusted under 35 U.S.C. 154(b) by 937 days.

(21) Appl. No.: 17/142,694

(22) Filed: Jan. 6, 2021

(65) Prior Publication Data

US 2022/0211922 A1   Jul. 7, 2022

(51) Int. Cl.
| | |
|---|---|
| A61L 31/16 | (2006.01) |
| A61F 2/00 | (2006.01) |
| A61K 9/00 | (2006.01) |
| A61K 31/137 | (2006.01) |
| A61K 31/195 | (2006.01) |
| A61K 31/496 | (2006.01) |
| A61K 31/65 | (2006.01) |
| A61K 31/717 | (2006.01) |
| A61K 31/722 | (2006.01) |
| A61K 45/06 | (2006.01) |

(Continued)

(52) U.S. Cl.
CPC ............ *A61L 31/16* (2013.01); *A61K 9/0024* (2013.01); *A61K 31/137* (2013.01); *A61K 31/195* (2013.01); *A61K 31/496* (2013.01); *A61K 31/65* (2013.01); *A61K 31/717* (2013.01); *A61K 31/722* (2013.01); *A61K 45/06* (2013.01); *A61K 47/42* (2013.01); *A61L 31/044* (2013.01); *A61L 31/10* (2013.01); *A61F 2/0077* (2013.01); *A61F 2250/0067* (2013.01); *A61L 33/18* (2013.01); *A61N 1/37518* (2017.08)

(58) Field of Classification Search
None
See application file for complete search history.

(56) References Cited

U.S. PATENT DOCUMENTS

| | | |
|---|---|---|
| 5,207,709 A | 5/1993 | Picha |
| 7,795,027 B2 | 9/2010 | Hiles |

(Continued)

FOREIGN PATENT DOCUMENTS

| | | |
|---|---|---|
| EP | 1355588 B1 | 8/2007 |
| WO | 2019113451 A1 | 6/2019 |

OTHER PUBLICATIONS

Zieske, L. R., Hsi, K.-L., Chen, L., & Yuan, P.-M. (1992). Structural determination of the essential serine and glycosylation sites of carboxypeptidase P. Archives of Biochemistry and Biophysics, 295(1), 76-83. https://doi.org/10.1016/0003-9861(92)90490-n (Year: 1992).*

(Continued)

*Primary Examiner* — Christine H Matthews
*Assistant Examiner* — Marc D. Honrath
(74) *Attorney, Agent, or Firm* — Sorell, Lenna & Schmidt, LLP

(57) ABSTRACT

A surgical device configured to surround an implantable medical device that includes a collagen membrane and a coating embedded in the membrane, the coating including at least one active pharmaceutical ingredient.

16 Claims, 14 Drawing Sheets

(51) Int. Cl.
*A61K 47/42* (2017.01)
*A61L 31/04* (2006.01)
*A61L 31/10* (2006.01)
*A61L 33/18* (2006.01)
*A61N 1/375* (2006.01)

(56) References Cited

U.S. PATENT DOCUMENTS

| | | | |
|---|---|---|---|
| 8,696,744 B2 | 4/2014 | Matheny et al. | |
| 8,778,012 B2 | 7/2014 | Matheny | |
| 9,011,526 B2 | 4/2015 | Matheny | |
| 9,066,993 B2 | 6/2015 | Matheny | |
| 9,211,175 B2 | 12/2015 | Stopek et al. | |
| 10,293,084 B2 | 5/2019 | Matheny | |
| 10,420,864 B2 * | 9/2019 | Pulapura | A61L 31/04 |
| 10,980,922 B2 * | 4/2021 | Pulapura | A61L 31/10 |
| 2013/0023721 A1 * | 1/2013 | Matheny | A61P 31/00 |
| | | | 600/16 |
| 2017/0319755 A1 | 11/2017 | Pulapura et al. | |
| 2018/0272136 A1 | 9/2018 | Horn et al. | |
| 2019/0030218 A1 | 1/2019 | Pulapura et al. | |
| 2019/0262510 A1 | 8/2019 | Chen et al. | |
| 2019/0351241 A1 * | 11/2019 | Novak | A61L 31/146 |

OTHER PUBLICATIONS

Thiede, B., Wittmann-Liebold, B., Bienert, M., & Krause, E. (1995). MALDI-MS for c-terminal sequence determination of peptides and proteins degraded by carboxypeptidase Y and p. FEBS Letters, 357(1), 65-69. https://doi.org/10.1016/0014-5793(94)01323-s (Year: 1995).*

PCT International Search Report, Name and mailing address of the ISA: European Patent Office, P.B. 5818 Patentlaan 2 NL—2280 HV Rijswijk, International application No. PCT/US2021/063459, Date of mailing of the international search report Mar. 22, 2022.

PCT Written Opinion of the International Searching Authority, Name and mailing address of the ISA: European Patent Office, P.B. 5818 Patentlaan 2, NL-2280 HV Rijswijk, International application No. PCT/US2021/063459, Date of mailing of the international search report Mar. 22, 2022.

* cited by examiner

SURGICAL SYSTEM AND METHODS OF USE

TECHNICAL FIELD

The present disclosure generally relates to anchorage devices and methods configured for anchoring an implantable medical device within a body, wherein the anchorage device comprises at least one hemostatic agent that is configured to elute over time.

BACKGROUND

Some known anchorage devices may be used to secure an implantable medical device within a body of a patient. The anchorage device and implantable medical device can be inserted into a desired location within the body of the patient. The anchorage device can be used to help anchor or support the implantable medical device to surrounding tissue. Some known anchorage devices are used to provide temporary support to tissue during a healing process. For example, some known anchorage devices can secure one portion of tissue to another portion of tissue.

Infection and bleeding are the most serious complications after surgery. The estimated increase in costs due to surgical site infections (SSIs) was $11,876 for SSIs overall ($7003 for superficial and $25,721 for deep infections). However, within the current $6 billion hemostat market, there are few produces that can address this unmet need. It would therefore be desirable to stop or reduce the flow of blood at a surgical site and/or speed up the blood clotting process while anchoring the implantable medical device to tissue. This disclosure describes an improvement over these prior art technologies.

SUMMARY

New anchorage devices and methods are provided to help anchor or support an implantable medical device to surrounding tissue. In one embodiment, in accordance with the principles of the present disclosure, a surgical system comprises an implantable medical device having a size and shape. A surgical device comprises a substrate and a coating that covers at least a portion of the substrate. The coating comprises collagen, glycerin and a hemostatic agent. The substrate comprises a first piece and a second piece that is joined with the first piece. The first piece and the second piece form a pocket having a cavity and an opening that is in communication with the cavity. The device is pre-formed such that a size and shape of the cavity conforms to the size and shape of the implantable medical device.

In one embodiment, in accordance with the principles of the present disclosure, a surgical system comprises a package including an aperture and an insert positioned within the aperture. An implantable medical device has a size and shape. The implantable medical device is an implantable device such as pulse generator (IPG) or diagnostic device. Example of such devices include a pacemaker or a cardioverter-defibrillator. A surgical device comprises a substrate and a coating that covers at least a portion of the substrate. The coating comprises collagen, glycerin and a hemostatic agent. The collagen includes carboxypeptidase collagen (CPP collagen) or carboxypeptidase X collagen (CPX collagen). The substrate comprises a first piece and a second piece that is joined with the first piece. The first piece and the second piece form a pocket having a cavity and an opening that is in communication with the cavity. The device is pre-formed such that a size and shape of the cavity conforms to the size and shape of the implantable medical device. The insert is positioned in the cavity to maintain the size and shape of the cavity.

In one embodiment, in accordance with the principles of the present disclosure, a surgical system comprises a package including an aperture and an insert positioned within the aperture. An implantable medical device has a size and shape. The implantable medical device is a pacemaker or a cardioverter-defibrillator. A surgical device comprises a substrate and a coating that covers at least a portion of the substrate. The coating comprises collagen, glycerin and a hemostatic agent. The collagen includes CPP collagen or CPX collagen. The substrate comprises a first piece and a second piece that is joined with the first piece. The first piece and the second piece form a pocket having a cavity and an opening that is in communication with the cavity. The device is pre-formed such that a size and shape of the cavity conforms to the size and shape of the implantable medical device. The implantable medical device is positioned in the cavity. The insert is configured to be positioned in the cavity to maintain the size and shape of the cavity.

In one embodiment, in accordance with the principles of the present disclosure, a method of manufacturing a surgical device comprises: providing a substrate having opposite first and second sides, the second side having a first section and a second section; coupling a substrate to a fixture such that the first side faces the fixture; and depositing a gel onto the second side such that the gel coats the first section without coating the second section In one embodiment, in accordance with the principles of the present disclosure, a method of manufacturing a surgical device comprises: providing a substrate having opposite first and second sides, the second side having a first section and a second section, wherein the substrate is an absorbable antibacterial envelope; coupling a substrate to a fixture such that the first side faces the fixture; and 3D printing a gel onto the second side such that the gel coats the first section without coating the second section. Wherein the first section comprises a plurality of first sections that are spaced apart from one another by the second section. In some embodiments, the gel consists of trans-4-(aminomethyl)cyclohexanecarboxylic acid ($C_8H_{15}NO_2$) suspended in a solution, the solution consisting of collagen, water and glycerol. In some embodiments, the gel consists of trans-4-(aminomethyl)cyclohexanecarboxylic acid (C8H15NO2) suspended in a solution, the solution consisting of an alginate, water and glycerol.

In one embodiment, in accordance with the principles of the present disclosure, a method of manufacturing a surgical device comprises: providing a substrate having opposite first and second sides, the second side having a first section and a second section, wherein the substrate is an absorbable antibacterial envelope; coupling a substrate to a fixture such that the first side faces the fixture; and depositing a gel onto the second side using a robot such that the gel coats the first section without coating the second section. Wherein the first section comprises a plurality of first sections that are spaced apart from one another by the second section. Wherein the gel consists of trans-4-(aminomethyl)cyclohexanecarboxylic acid ($C_8H_{15}NO_2$) suspended in a solution, the solution consisting of collagen, water and glycerol In one embodiment, in accordance with the principles of the present disclosure, a method of manufacturing a surgical device comprises: providing a substrate having opposite first and second sides; coupling a substrate to a plate such that the first side faces the plate; and spraying a coating onto the second side.

In one embodiment, in accordance with the principles of the present disclosure, a method of manufacturing a surgical device comprises: providing a plate; coupling a polyimide liner directly to a planar surface of the plate; coupling a mesh substrate to the liner such that a first side of the substrate faces the liner and an opposite second side of the plate faces away from the liner; positioning a hold down feature over the substrate to prevent movement of the substrate relative to the plate; spraying a coating onto the second side such that the coating fills interstitial spaces of the mesh without the coating passing through the first side, the coating comprising collagen, glycerin and a hemostatic agent; and cooling the plate.

In one embodiment, in accordance with the principles of the present disclosure, a method of manufacturing a surgical device comprises: providing a plate; coupling a polyimide liner directly to a curved surface of the plate; coupling a mesh substrate to the liner such that a first side of the substrate faces the liner and an opposite second side of the plate faces away from the liner; positioning a hold down feature over the substrate to prevent movement of the substrate relative to the plate; spraying a coating onto the second side such that the coating fills interstitial spaces of the mesh without the coating passing through the first side, the coating comprising collagen, glycerin and a hemostatic agent; and cooling the plate.

In one embodiment, in accordance with the principles of the present disclosure, a package for a surgical implant comprises a body having a side wall including opposite top and bottom ends. The body comprises a bottom wall coupled to the bottom end. The body includes a flange extending outwardly from the top end. Inner surfaces of the walls define a cavity. The top end defines an opening that is in communication with the cavity. An insert extends from the bottom wall such that the insert is positioned in the cavity. A lid is configured to be coupled to the flange such that the lid covers the opening.

In one embodiment, in accordance with the principles of the present disclosure, a surgical system comprises a package comprising a body having a side wall including opposite top and bottom ends. The body comprises a bottom wall coupled to the bottom end. Inner surfaces of the walls define a first cavity. The top end defines a first opening that is in communication with the first cavity. An insert extends from the bottom wall such that the insert is positioned in the first cavity. The insert has a size and shape. A surgical device comprises a substrate comprising a first piece and a second piece that is joined with the first piece. The first piece and the second piece form a pocket having a second cavity and a second opening that is in communication with the second cavity. The device is pre-formed such that a size and shape of the second cavity conforms to the size and shape of the insert.

In one embodiment, in accordance with the principles of the present disclosure, a surgical system comprises a package comprising a body having a side wall including opposite top and bottom ends. The body comprises a bottom wall coupled to the bottom end. Inner surfaces of the walls define a first cavity. The top end defines a first opening that is in communication with the first cavity. An insert extends from the bottom wall such that the insert is positioned in the first cavity. The insert has a size and shape defined by opposite first and second side walls of the insert that each extend from a top wall of the insert to an opposite bottom wall of the insert. The top wall is convexly curved from the first side wall to the second side wall. The first side wall extends parallel to the second side wall from the top wall to the bottom wall of the insert. The insert includes opposite front and back walls that each extend from the top wall to the bottom wall of the insert and from the first side wall to the second side wall. The front wall extends parallel to the back wall from the top wall to the bottom wall of the insert. A surgical device comprises a substrate comprising a first piece and a second piece that is joined with the first piece. The first piece and the second piece form a pocket having a second cavity and a second opening that is in communication with the second cavity. The device is pre-formed such that a size and shape of the second cavity conforms to the size and shape of the insert. The device comprises a coating that covers at least a portion of the substrate. The coating consists of collagen, glycerin and trans-4-(aminomethyl) cyclohexanecarboxylic acid ($C_8H_{15}NO_2$)

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which.

DETAILED DESCRIPTION

Figure 1:
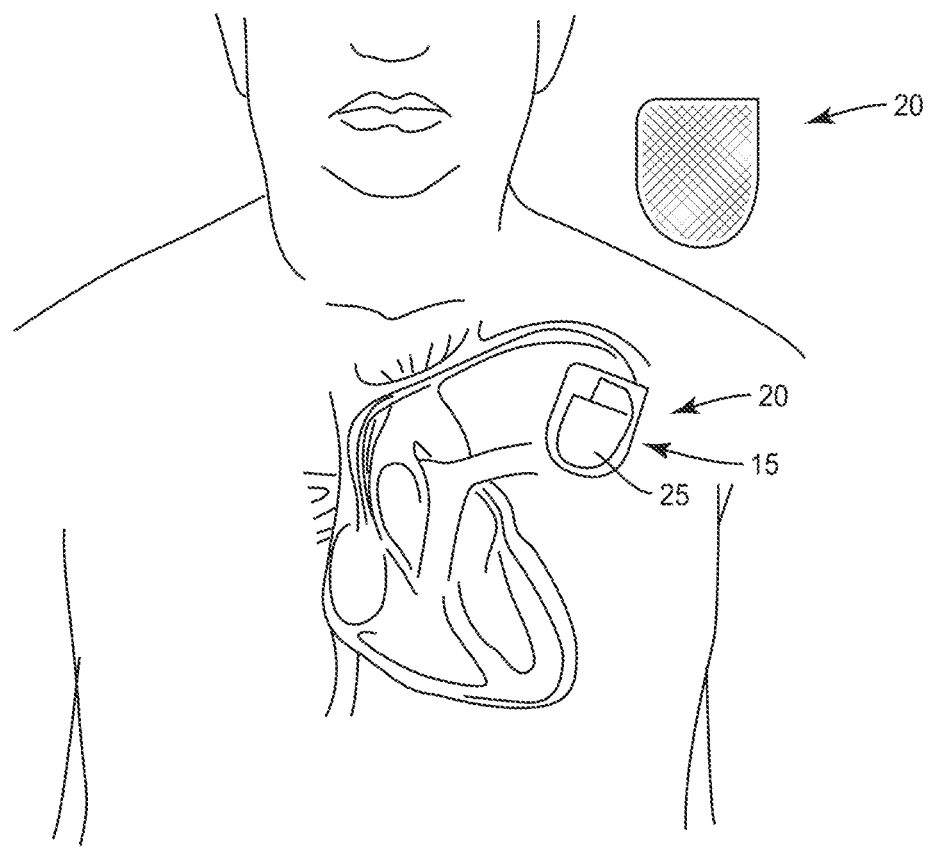
FIG. 1 is a plan view of components of a surgical system, in accordance with the principles of the present disclosure.

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Surgical site infections are increasing in frequency, severity and cost. Antibiotics are effective in eliminating short term infection at surgical sites. However, their effectiveness in preventing biofilms is poor, long term infections remain problematic and they often are effective only on a subset of the pathogens and can cause bacterial resistance. This disclosure provides a fundamental shift in the thinking of how to address infection by providing a new approach that can lead to better infection prevention outcomes, better overall healing and eliminate or minimize the use of antibiotics.

This disclosure is directed to a surgical system that includes one or more active pharmaceutical ingredients together with one or more hemostatic agents in order to prevent or reduce bleeding via the one or more hemostatic agents and provide another effect, such as, for example, an antimicrobial effect via the one or more hemostatic agents. In some embodiments, a coating that includes one or more active pharmaceutical ingredients together with one or more hemostatic agents is applied to a substrate to coat at least a portion of the substrate to prevent bacterial adhesion and form a defect-free conformal coating and/or a nanostructured anti-bacterial surface upon implantation of the substrate. In some embodiments, the coating includes a polymer that includes the one or more active pharmaceutical ingredients and the one or more hemostatic agents dispersed therein, as discussed herein. In some embodiments, the coating does not include a polymer and is synthesized either all or in part from the one or more active pharmaceutical ingredients and the one or more hemostatic agents, as discussed herein.

In some embodiments, the one or more active pharmaceutical ingredients and the one or more hemostatic agents are provided in a new polymeric coating that prevents bacterial adhesion and forms a defect-free conformal coating and/or a nanostructured anti-bacterial surface. In some embodiments, the coating is synthesized from antibacterial materials and have surface active groups such as carbohydrates in monomer or polymer form that stimulate an immune response to eliminate the bacteria or groups that attract growth factors for scar free healing. It is envisioned that the coating that eliminates the long term use of antibiotics. Eliminating the use of antibiotics can reduce the risk of developing antibiotics resistance bacterial.

In some embodiments, the one or more active pharmaceutical ingredients and the one or more hemostatic agents are provided in a powder that can be applied directly to a surgical site via a syringe or other delivery device, as discussed herein. The powder, that can both have hemostatic and antibacterial function, can be used with or without an anchorage device or other substrate that includes one or more active pharmaceutical ingredients together with one or more hemostatic agents.

This disclosure is directed to a surgical system that includes a new and easy-to-use products, such as, for example novel devices device coatings and powders that solve complications related to infection and/or bleeding by leveraging existing clinically proven TYRX antimicrobial technology (a tyrosine-derived polyarylate polymer that can be applied to a substrate and is configured to release one or more agents, such as, for example, antimicrobial agents, over time as the substrate anchors an implantable medical device within a patient) and Medtronic Minimally Invasive Technology Group (MITG) hemostatic technology containing oxidized cellulose substrate, (example product is Veriset). VERISET is made of oxidized cellulose coated with multiple arm PEG and triglycine. PEG and triglycine are functionalized and can react with each other upon wet, forming a hydrogel for stopping the bleeding. In addition, the oxidized cellulose can trigger clotting and platelet aggregation to provide hemostatic effect. The core technology in TYRX antimicrobial technology is the controlled drug release over extended period. The coating can be processed into a variety of form factors such as particles, then paste and gel. These particles can be used to make a product in powder form, while paste and gel can be further made from the powder. Paste and gel are preferred sometime as they are easily to control for application, or in the case here, a liquid that gels when deposited and cooled to a lower temperature. By mixing these particles into a hemostatic matrix, such as oxidized cellulose, it will create combinational coatings and other products for reducing bleeding and infection. Additionally, pain medications can be added easily such as bupivacaine.

In some embodiments, a TYRX antibacterial envelope is used to treat surgical site infections by delivery of two antibiotics. VERISET hemostat, used to control bleeding is made from oxidized cellulose and a PEG compound. A powder can be made from the coating of the TYRX envelope and oxidized cellulose in the VERISET. A power can also be made by grounding both the TYRX mesh and VERISET product.

In some embodiments, an anchorage device is provided that includes a substrate is in the form of an envelope. A coating coats at least a portion of the envelope, wherein the coating is made from drugs, such as, for example, antibacterial drugs, that are dispersed throughout a tyrosine polymer and oxidized cellulose.

Treatments for infection control and bleeding are available. This disclosure is directed to a surgical system that provides a way to treat both complications (infections and bleeding) simultaneously, by delivering the hemostat and antibiotics together. In some embodiments, the surgical system includes a TYRX antibacterial envelope that is used to treat surgical site infections by delivery of two antibiotics and a VERISET hemostat that is used to control bleeding. In some embodiments, the VERISET hemostat is made from oxidized cellulose and a PEG compound. In some embodiments, the envelope is processed into a first powder and the VERISET hemostat is processed into a second powder. The first and second powders are combined. Other components are added to the combined first and second powders to form a coating and/or other products configured to simultaneously treat and/or prevent infection and bleeding.

In some embodiments, the surgical system has a hemostatic and antibacterial dual function, as discussed herein. In some embodiments, the surgical system includes components that are easy to deliver. In some embodiments, the surgical system includes components that are FDA cleared. In some embodiments, the surgical system includes components that have no known interaction between them. In some embodiments, the surgical system is easy to manufacture. In some embodiments, the surgical system includes a convenient delivery system. In some embodiments, the surgical system is readily adaptable to different drugs. In some embodiments, absorption time can be tuned depending upon application. In some embodiments, animal models can be used to test efficacy. In some embodiments, the surgical system will have a minimal impact on surgery time.

In some embodiments, this disclosure is directed to a surgical system that includes coatings and/or other products that include powders of one or more antibacterial drugs in tyrosine polymers. In some embodiments, coatings and/or other products include powders of one or more antibacterial drugs in oxidized cellulose.

In some embodiments, a collagen and glycerol coating containing TXA is applied to an TYRX envelope to raise its efficacy by preventing excessive hemorrhaging in the pocket formed for the implanted device such as a pacer or an cardioverter-defibrillator, etc. The TXA may also be applied to TYRX type patches that are cut to size for given application and operation and are employed in operations where bleeding control is desirable or necessary.

This disclosure is further directed to a method for depositing a novel coating on an implant or other device to simultaneously treat and/or prevent infection and bleeding. In some embodiments, the method includes depositing the coating on a substrate using a robotically controlled gel dispensing system. In some embodiments, the method includes depositing rows or other shapes on a mesh, wherein the mesh can be backed or unbacked. In some embodiments, multiple tip printing is utilized to provide multiple colors. In some embodiments, the method includes depositing 3D shapes of the coating on a substrate. In some embodiments, the method includes leaving selected portion(s) of the substrate uncovered (not coated with the covering) to provide for better handling in the operating room. In some embodiments, the gel coating that is deposited on the substrate includes TXA suspended in a collagen, water, and glycerol solution.

This disclosure is further directed to a method for depositing a novel coating on an implant or other device to simultaneously treat and/or prevent infection and bleeding. In some embodiments, the coating is a collagen and glycerol coating containing tranexamic acid, wherein the coating is applied to implants, such as, for example, surgical meshes. In some embodiments, the method includes depositing the coating on a substrate such that the coating forms selected custom shapes, such as, for example, squares, rectangles, etc. where bleeding control is desirable or necessary (soft tissue). In some embodiments, the method includes spraying droplets such that an uneven concentration of the coating is formed as the coating impacts the substrate. In some embodiments, the method ensures even wetting. In some embodiments, the method includes a plate, or shape, that contacts substrate in areas where the coating will be deposited. This reflow/wetting of the substrate (mesh) and the backing structure (plate, drum, half pipe, etc.) ensures even distribution and filling of interstitial spaces (porosity) of the substrate (mesh). In addition, the backing structure ensures capture of all of the spray rather than letting some pass through the openings in the substrate such as knit mesh.

In some embodiments, the disclosed surgical system includes packaging to transport an implant of the surgical system, such as, for example a coated mesh substrate from the manufacturer to a physician. Indeed, in that mesh substrates tend to become more rigid after they are coated, the mesh substrates are typically immersed in saline, for example, in order to wet the mesh substrate so that the mesh substrate becomes pliable enough to insert an implantable medical device, such as, for example, a pacemaker into the mesh substrate. However, the duration of the immersion has been proven difficult to predict and/or control. As such, in some embodiments, the disclosed surgical system includes a device, such as, for example, a mesh substrate that is pre-formed to have a selected shape while the mesh substrate is coated, wherein the selected shape matches the shape of the implantable medical device to allow the implantable medical device to be inserted into the mesh substrate without wetting the mesh substrate or stretching/manipulating the mesh substrate to fit the implantable medical device within the mesh substrate. The packaging of the disclosed surgical system is configured to maintain the pre-formed shape of the mesh substrate as the mesh substrate is transported from the manufacturer to a physician. In some embodiments, the packaging has a thermally formed shape. In some embodiments, the package includes a desiccant, a thermally sealed top flange and/or is sterilized.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

This disclosure is directed to a surgical system 15. In some embodiments, system 15 includes one or more anchorage devices, such as, for example, an anchorage device 20. In some embodiments, the components of anchorage device 20 can be fabricated from biologically acceptable materials suitable for medical applications, including metals, synthetic polymers, allografts, xenografts, isografts, ceramics and bone material and/or their composites, depending on the particular application and/or preference of a medical practitioner. For example, the components of anchorage device 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, tyrosine polyarylate, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polylactide, polyglycolide, polytyrosine carbonate, polycaprolactone and their combinations.

Various components of anchorage device 20 may have material composites, including the above materials, to achieve various desired characteristics such as strength, rigidity, elasticity, compliance, biomechanical performance, durability and radiolucency or imaging preference. The components of anchorage device 20, individually or collectively, may also be fabricated from a heterogeneous material such as a combination of two or more of the above-described materials. The components of anchorage device 20 may be monolithically formed, integrally connected or include fastening elements and/or instruments, as described herein.

Anchorage device 20 includes a substrate, such as, for example, substrate 22. Substrate 22 is configured to be coupled to and/or applied to a device, such as, for example, a medical device 25. In some embodiments, medical device 25 is an implantable medical device, as discussed herein. In some embodiments, medical device 25 is a non-implantable medical device, as discussed herein. In some embodiments, substrate 22 is configured to surround and/or enclose at least a portion of medical device 25, as discussed herein. Substrate 22 is configured to be secured to tissue to support one or more devices 25, such as grafts (e.g., abdominal aortic aneurysm grafts, etc.), stents, catheters (including arterial, intravenous, blood pressure, stent graft, etc.), valves (e.g., polymeric or carbon mechanical valves), embolic protection filters (including distal protection devices), vena cava filters, aneurysm exclusion devices, artificial hearts, cardiac jackets, and heart assist devices (including left ventricle assist devices), implantable defibrillators, subcutaneous implantable defibrillators, implantable monitors, for example, implantable cardiac monitors, electrostimulation devices and leads (including pacemakers, lead adapters and lead connectors), implanted medical device power supplies, peripheral cardiovascular devices, atrial septal defect closures, left atrial appendage filters, valve annuloplasty devices, mitral valve repair devices, vascular intervention devices, ventricular assist pumps, and vascular access devices (including parenteral feeding catheters, vascular access ports, central venous access catheters).

Implantable medical devices may also include, for example, surgical devices such as sutures of all types, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps. Implantable medical devices may also include, for example, orthopedic devices such as joint implants, acetabular cups, patellar buttons, bone repair/augmentation devices, spinal devices (e.g., vertebral disks and the like), bone pins, cartilage repair devices, and artificial tendons. Implantable medical devices may also include, for example, dental devices such as dental implants and dental fracture repair devices. Implantable medical devices may also include, for example, drug delivery devices such as drug delivery pumps, implanted drug infusion tubes, drug infusion catheters, and intravitreal drug delivery devices. Implantable medical devices may also include, for example, ophthalmic devices such as scleral buckles and sponges, glaucoma drain shunts and intraocular lenses.

Implantable medical devices may also include, for example, urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices. Implantable medical devices may also include, for example, synthetic prostheses such as breast prostheses and artificial organs (e.g., pancreas, liver, lungs, heart, etc.). Implantable medical devices may also include, for example, respiratory devices including lung catheters. Implantable medical devices may also include, for example, neurological devices such as neurostimulators, neurological catheters, neurovascular balloon catheters, neuro-aneurysm treatment coils, and neuropatches, splints, ear wicks, ear drainage tubes, tympanostomy vent tubes, otological strips, laryngectomy tubes, esophageal tubes, esophageal stents, laryngeal stents, salivary bypass tubes, and tracheostomy tubes. Implantable medical devices may also include, for example, oncological implants. Implantable medical devices may also include, for example, pain management implants.

In some embodiments, substrate 22 is configured to be coupled to and/or applied to or to surround and/or enclose at least a portion of a non-implantable medical device, as discussed herein. Non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dilators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dilators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

Substrate 22 can have a variety of different configurations, shapes and sizes. For example, substrate 22 can be provided with a size and shape or other configuration that can provide the functionality of supporting and immobilizing the medical device 25 at a treatment site within a patient's body, while also improving the removability of anchorage device 20 after the treatment has been completed. In some embodiments, medical device 25 can be disposed within a pocket defined by substrate 22 and anchorage device 20 can be implanted and secured to tissue at a desired treatment site within a body of a patient. As discussed herein, during implantation, scar tissue can form at the treatment site and/or tissue can become ingrown within substrate 22. After the treatment is completed, medical device 25 can remain in the patient as discussed below or can be removed from the patient leaving anchorage device 20 implanted. To remove anchorage device 20, tissue that is ingrown within substrate 22 can be cut or otherwise detached from substrate 22. In some embodiments, a portion of anchorage device 20 may not be removable from the tissue and will remain implanted within the patient.

Substrate 22 may be formed with one or more biocompatible materials, which may be synthetic or naturally occurring. In some embodiments, the one or more biocompatible materials include, for example, polypropylene, polyester, polytetrafluoroethylene, polyamides, silicones, polysulfones, metals, alloys, titanium, stainless steel, shape memory metals (e.g. Nitinol), and/or combinations thereof. In some embodiments, substrate 22 is made at least in part from one or more hemostatic agents, such as, for example, collagen. In some embodiments, substrate 22 is made entirely from a hemostatic agent, such as, for example, collagen. In some embodiments, substrate 22 is free of any hemostatic agents such that any hemostatic of device 20 would be included in a coating that coats substrate 22, rather from substrate 22 itself.

In some embodiments, substrate 22 is configured to be implanted temporarily within a body of a patient and/or is configured to be removed (e.g., explanted) from the patient's body after a period of time. In such embodiments, substrate 22 may include a non-biodegradable material and/or a non-bioresorbable material. For example, substrate 22 may be made entirely from a non-biodegradable material and/or a non-bioresorbable material such that substrate 22 is made only from the non-biodegradable material and/or non-bioresorbable material. In some embodiments, substrate 22 may include one or more non-biodegradable and/or a non-bioresorbable material and one or more biodegradable and/or resorbable material. In some embodiments, one side of substrate 22 may include one or more non-biodegradable and/or a non-bioresorbable material and another side of substrate 22 can include one or more biodegradable and/or resorbable material.

As used herein, the term "biodegradable" refers to, for example, a material that can be at least partially broken down or degraded by a bodily fluid and discarded as waste from the body and/or a material that can be broken down or degraded by a living organism. Thus, "non-biodegradable" can refer to a material that cannot be broken down or degraded by a bodily fluid and/or cannot be broken down or degraded by a living organism. As used herein the term "resorbable" refers to, for example, a material that can be at least partially broken down or degraded by a bodily fluid and assimilated within the body. Thus, a "non-resorbable" material as used herein can refer to, for example, a material that cannot be broken down or degraded by bodily fluid and assimilated within the body.

In some embodiments, the biocompatible biodegradable and/or bioresorbable material or materials may include polymeric and/or non-polymeric materials, such as, for example, one or more poly (alpha-hydroxy acids), poly (lactide-co-glycolide) (PLGA), polylactide (PLA), poly(L-lactide), polyglycolide (PG), polyethylene glycol (PEG) conjugates of poly (alpha-hydroxy acids), polyorthoesters (POE), polyaspirins, polyphosphazenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyrrolidone, polyamide, oxycellulose, copolymer of glycolic acid and trimethylene carbonate, polyesteramides, tyrosine polyarylates, polyetheretherketone, polymethylmethacrylate, silicone, hyaluronic acid, chitosan, or combinations thereof. In one embodiment, substrate 22 comprises Glycoprene, which is sold by Poly-Med, Inc. As used herein, the term "glycoprene" or "Glycoprene" refers to Glycoprene® or Glycoprene II®. Glycoprene® can refer to different variations of the material sold under the trade name Glycoprene®, such as, for example, Glycoprene®6829, Glycoprene®8609 and Glycoprene® 7027.

In some embodiments, the biocompatible non-biodegradable and/or non-bioresorbable material or materials may include polymeric and/or non-polymeric materials, such as, for example, polyurethane, polyester, polytetrafluoroethylene (PTFE), polyethylacrylate/polymethylmethacrylate, polylactide, polylactide-co-glycolide, polyamides, polydioxanone, polyvinyl chloride, polymeric or silicone rubber, collagen, thermoplastics, or combinations thereof.

In some embodiments, substrate 22 is configured to be permanently implanted within a body of a patient. In such embodiments, substrate 22 may include a biodegradable material and/or a bioresorbable material. For example, substrate 22 may be made entirely from a biodegradable material and/or a bioresorbable material such that substrate 22 is made only from the biodegradable material and/or bioresorbable material.

In some embodiments, substrate 22 is provided in the form of a mesh. In some embodiments, the mesh is web or fabric with a construction of knitted, braided, woven or non-woven filaments or fibers that are interlocked in such a way to create a fabric or a fabric-like material that includes a matrix of filaments that define multiple pores. That is, the space between adjacent filaments or fibers define pores of the mesh. Pores may be beneficial to allow tissue in-growth, for example. In some embodiments, apertures may be formed in the mesh by cutting the filaments or fibers to decrease the areal density (e.g., surface density) or mass of the mesh and/or further facilitate tissue in-growth. In some embodiments, the apertures that extend through the filaments or fibers are larger than pores defined by the filaments or fibers.

In some embodiments, substrate 22 is provided in the form of a thin walled structure, such as, for example, a wafer, sheet or tissue. In some embodiments, the thin walled structure does not include any pores or apertures, in contrast to the mesh discussed herein. In some embodiments, the thin walled structure includes pores or apertures that are smaller than the pores or apertures of the mesh discussed herein. In some embodiments, the thin walled structure has a thickness that is less than a thickness of the mesh discussed herein. In some embodiments, the thickness of the thin walled structure is between about 0.001 inches and about 0.1 inches.

In some embodiments, anchorage device 20 includes an overlay, such as, for example, a coating 24 that is applied to substrate 22 such that coating 24 covers all or a portion of substrate 22. In some embodiments, coating 24 can be processed into a variety of form factors such as particles, then paste and gel. The particles may be mixed into a hemostatic matrix that comprises oxidized cellulose, for example.

In some embodiments, coating 24 includes collagen, glycerol and TXA and is configured to be applied directly to substrate 24. In some embodiments, the coating comprises between about 0.1 wt % and about 10 wt % collagen, between about 90 wt % and about 99 wt % water, between about 0.1 wt % and about 3.0 wt % glycerol, between about 0.1 wt % and about 5.0 wt % TXA and between about 0.1 wt % and about 8.0 wt % 1N NaOH. In some embodiments, the coating comprises between about 1.2 wt % and about 5.4 wt % collagen, between about 87.1 wt % and about 97.1 wt % water, between about 0.2 wt % and about 2.2 wt % glycerol, between about 0.1 wt % and about 2.0 wt % TXA and between about 0.3 wt % and about 4.3 wt % 1N NaOH.

In some embodiments, the coating comprises about 3.4 wt % collagen, about 92.1 wt % water, about 1.2 wt % glycerol, about 0.9 wt % TXA and about 2.3 wt % 1N NaOH. In some embodiments, the coating comprises 3.4 wt % collagen, 92.1 wt % water, 1.2 wt % glycerol, 0.9 wt % TXA and 2.3 wt % 1N NaOH. In some embodiments, water may be reduced by up to a factor of 10.

In some embodiments, coating 24 can include one or more hemostatic agent (HA) and/or one or more active pharmaceutical ingredient (API). In some embodiments, coating 24 is free of any polymer such that the HA and the API are applied directly to substrate 22 in the form of a powder, for example. In some embodiments, the HA and the API are dispersed within a polymer, such as, for example, one or more of the polymers discussed herein such that the polymer degrades to release the HA and the API upon implantation of device 20. In some embodiments, substrate 22 is biodegradable and/or bioresorbable and device 20 is configured to hold medical device 25 therein such that substrate 22 does not begin to degrade until the polymer completely degrades such that device 20 can hold medical device 25 therein until all of the HA and the API are released from the polymer. In some embodiments, substrate 22 is completely biodegradable or bioresorbable. That all of substrate 22 is biodegradable or bioresorbable. In some embodiments, substrate 22 is completely non-biodegradable and/or non-bioresorbable. That is no portion of substrate 22 is biodegradable or bioresorbable.

The HA can include one or more hemostatic agents, such as, for example, epinephrine, tranexamic acid, collagen, chitosan and oxidized regenerated cellulose. In some embodiments, the collagen can include acid soluble collagen, pepsin soluble collagen, gelatin, cross-linkable collagen, fibrillar collagen. In some embodiments, the HA can include one or more of Spongostan®, Surgifoam®, Avitene, thrombin and Ostene® in addition to or in place of the hemostatic agents discussed above. In some embodiments, the HA can include one or more of protamine, norepinephrine, desmopressin, lysine analogs, gelatin, polysaccharide spheres, mineral zeolite, bovine thrombin, pooled human thrombin, recombinant thrombin, gelatin and thrombin, collagen and thrombin, cyanacrylate, fibrin glue, polyethylene glycol, and glutaraldehyde in addition to or in place of the hemostatic agents discussed above. In some embodiments, the HA includes a mixture or combination of the HAs discussed herein. In some embodiments, the lysine analog is tranexamic acid and has the formula:

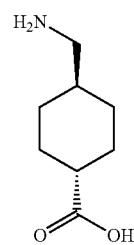

In some embodiments, the anchorage devices disclosed herein utilize one or more pharmacologic hemostatic agent since pharmacologic hemostatic agents have been found to be desirable over mechanical hemostats for a variety of reasons. Ethnographic research has showed that physicians desire a hemostat that can provide an extended elution profile to reduce bleeding events for up to 7 days post operatively. Furthermore, there is a possible effect on handling and/or allergic reactions if mechanical hemostats, such as, for example, oxidized reduced cellulose or chitosan were used.

In some embodiments, tranexamic acid is preferred for use as the HA. Tranexamic acid is a synthetic analog of the amino acid lysine with a molecular weight of 157 g/mol. Tranexamic acid is an antifibrinolytic agent that acts by binding to plasminogen and blocking the interaction of plasminogen with fibrin, therefore preventing the dissolution of a fibrin clot. In the presence of a wound, fibrinolysis occurs naturally when a lysine residue such as tissue plasminogen activator (tPA), binds to plasmin causing the clot to lyse (or break). Tranexamic acid blocks tPA and keeps the clot from breaking, thus preventing unwanted bleeding.

Prior to a damaged endothelium, tPA is inhibited in the blood by plasminogen activator inhibitor/type 1 (PAI-1). Once damage occurs, the tPA is released slowly into the blood, activating fibrinolysis. Excessive fibrinolysis results in a condition called hyperfibrinolysis, which requires intervention such as fibrinogen, plasma, transfusion or antifibrinolytic therapy, such as tranexamic acid.

Tranexamic acid has been used for over 40 years to reduce bleeding complications. Tranexamic acid is most commonly given systemically at doses of 10 mg/kg followed by infusion of 10 mg/kg/h. Since 2007, tranexamic acid has received widespread approval and clinical use as a hemostatic agent. Knowing that surgical trauma causes fibrinolysis in the area of the surgical wound itself, topical antifibrinolytic therapy is becoming more common to obtain and maintain hemostasis. Clinical trials with topical tranexamic acid use exist for cardiac surgery, CIED procedures, orthopedic surgery, spinal surgery, dental extraction and epistaxis, and breast mammoplasty.

To evaluate the efficacy of tranexamic acid, a non-GLP acute porcine study was conducted. Doses of 1 mg to 200 mg of tranexamic acid were used in an in vitro whole blood coagulation test, a hepatic biopsy test, and a subcutaneous ICD surgical procedure.

The in vitro whole blood coagulation test showed no activity for tranexamic acid up to 10 mg/ml. The maximum tranexamic acid concentration, 200 mg/5 ml, was a slightly higher dose than that used clinically in a CIED pocket if 50 cc is the assumed blood volume of interest. Coagulation time was doubled with this higher dose.

The hepatic biopsy test had a volume of 0.016 ml when the biopsy hole was filled with blood. The minimum tranexamic acid dose evaluated was 2.5 mg, which is equivalent to 156 mg/ml. This concentration prevents blood from clotting quickly and these biopsies continued to bleed past the endpoint of 10 minutes. This phenomenon is likely due to the multiple bonding sites available to tranexamic acid in whole blood, and the fact that a biopsy does not induce fibrinolysis.

The subcutaneous surgical site test was conducted with an elevated ACT using heparin to induce hematoma. Surgical trauma similar to that of a CIEO implant was incurred in each pocket, but some subcutaneous pockets incurred more trauma than others due to anatomical location. The primary output monitored was accumulated blood as measured by pre-weighed gauze 3-hours post-operatively. With only one animal, and two pockets per treatment, the sample size was too low to show any significance between ICD only, ICD+ polymer, and ICD+polymer+tranexamic acid.

The non-GLP acute porcine study showed that in the dose range evaluated, tranexamic acid has a two-fold increase on clotting time and no effect on reducing bleeding on the hepatic biopsies. In the heparinized ICD pocket procedure, 3.5-22.8 grams of blood accumulated in a 3-hour period of time regardless of treatment. It appears that subcutaneous pockets in an anticoagulated porcine model would be a translatable model for evaluating efficacy of tranexamic acid because it has a relevant volume of accumulated blood and surgical trauma similar to that of a CIED procedure.

Based upon the non-GLP acute porcine study, tranexamic acid concentrations of 3.00 mg/L to 30 mg/L are effective in preventing fibrinolysis. As such, in some embodiments, the HA is tranexamic acid and is provided in concentrations of about 3.00 mg/L to about 30 mg/L. However, it has been found that one tenth of the doses used in the non-GLP acute porcine study can be effective in reversing fibrinolysis. As such, in some embodiments, the HA is tranexamic acid and is provided in concentrations of about 0.30 mg/L to about 3.0 mg/L for intravenous applications. In some embodiments, tranexamic acid is provided in concentrations of about 3.78 mg/L to about 30 mg/L for topical applications as well. However, in some embodiments, however, higher doses of tranexamic acid are used for topical applications to account for tranexamic acid being widely distributed throughout the extracellular and intracellular compartments when given preoperatively. Indeed, it has been found that tranexamic acid reaches plasma concentrations in 5-15 minutes. As such, in some embodiments, tranexamic acid is provided in doses of about 1.5 mg to about 150 mg.

Figure 5:
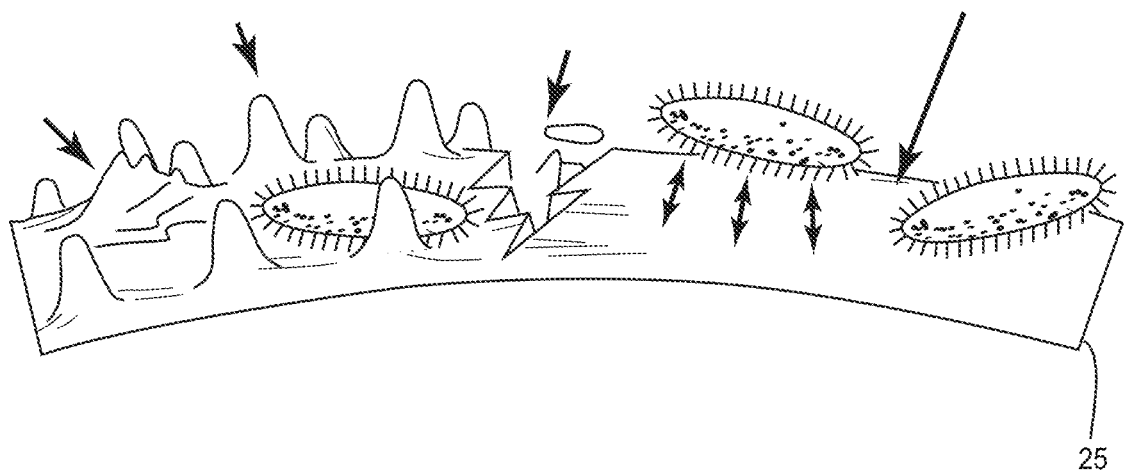
FIG. 5 is a perspective view of one embodiment of a component of the surgical system shown in FIG. 1, in accordance with the principles of the present disclosure.

FIG. 5 shows bacterial adhesion, or the lack thereof. In particular, FIG. 5 shows the microscopic surface of the fixation device containing a surface active group such a carbohydrates in a monomer or polymer form.

Figure 2:
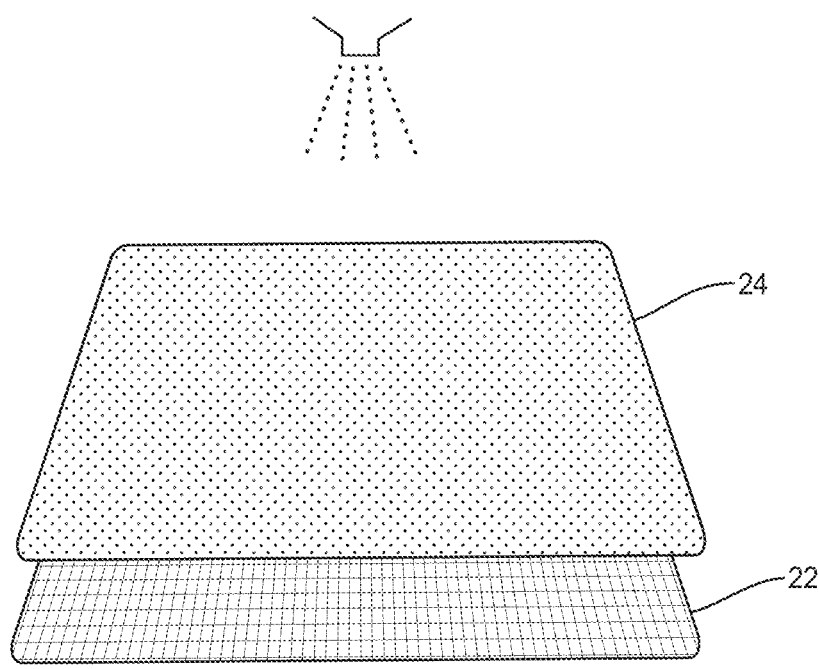
FIG. 2 is a perspective view showing one embodiment of making one embodiment of a component of the surgical system shown in FIG. 1, in accordance with the principles of the present disclosure.
Figure 6:
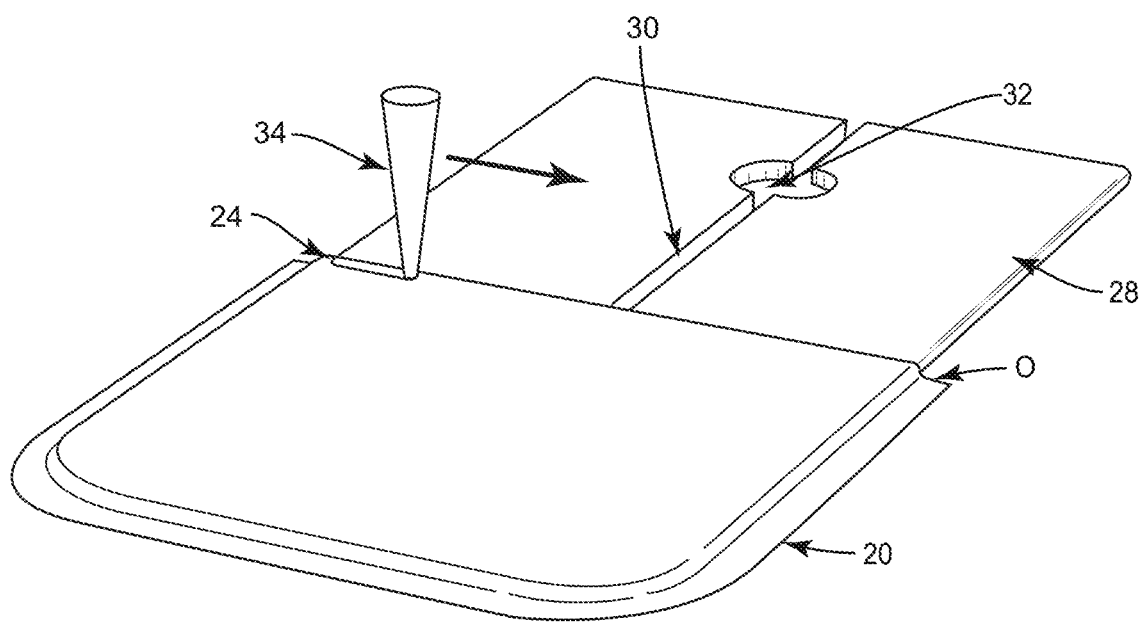
FIG. 6 is a perspective view showing one embodiment of making one embodiment of a component of the surgical system shown in FIG. 1, in accordance with the principles of the present disclosure.

In some embodiments, coating 24 may be applied to substrate 22 by spraying coating 24 onto substrate 22 (FIG. 2), coating all or a portion of substrate 22 with coating 24, or washing substrate 22 with coating 24. In some embodiments, coating 24 is in the form of a gel when coating 24 is applied to substrate 22. In particular, system 15 includes a robotically controlled gel dispensing system that applies coating 24 to substrate 22, as shown in FIG. 6. In some embodiments, substrate 22 is in the form of an envelope having an opening O into which a fixture or plate 28 of the robotically controlled gel dispensing system is inserted to position at least a portion of plate 28 within substrate 22 such that plate 28 is positioned between opposite first and second sides of the envelope. In some embodiments, plate 28 includes a single solid plate that is free of any openings or apertures that extend through a thickness of plate 28. In some embodiments, plate 28 includes a plate 28a and a plate 28b that is separated by a gap 30 and an aperture 32, as shown in FIG. 6. Coating 24 is dispensed by the robotically controlled gel dispensing system through a tip 34. In some embodiments, the fluid may be heated to promote flow and wetting characteristics. The substrate (TYRX pouch) and fixture in FIG. 6 may be cooled as low as −10 to −15 C to promote gelling and coating immobilization for subsequent handling. In some embodiments, the method includes coating the substrate with a warm coating material 40-60 C, allowing the coating material to gel on the cooled fixture and moving to the coated substrate to a drying oven/cabinet.

In some embodiments, the method described in the preceding paragraph is different and necessary from other methods due to the amount of coating that needs to be deposited. In some situations, the device will be pre-wetted in a saline solution just prior to implant to make the device slippery and easier to slip onto a tissue pocket. This wetting dissolves some of the coating and if the coating was thin, the relative amount of coating and drug content (TXA in this example) would be lost. If the coating is thick with same amount of TXA, less TXA would be lost in the same wetting process. The method described in the preceding paragraph has key advantages over other methods. For example, the coating has a necessary high volume of collagen to prevent loss of the hemostatic agent during implant. It could be imagined that concentration of the hemostatic agent (TXA) was so high that only a thin coating is necessary thus spraying or dipping could be imagined. Such a thin coating (10× thinner) is too vulnerable to the procedure involving pre-wetting the EZGlide envelope. Furthermore, coating rates are high variable but rates that have been used to date include 0.05 cc/up to 0.65 cc/s.

In some embodiments, the robotically controlled gel dispensing system applies coating 24 to substrate 22 without any fixture or plate, such as, for example, plate 28 being inserted into substrate 22.

In some embodiments, plate 28 provides several functions. For example, plate 28 acts a necessary backing plate that evenly distribute the coating solution by wetting out concentrations (drops) that would otherwise form a lose mesh. Plate 28 immediately cools the coating material allowing the solution to gel in place. Plate 28 provides a way to hold and flip the device to coat the other side. Plate 28 allows for transportation of the coated fixture and a method fixture for subsequent drying. Plate 28 may be coated with a non-stick coating such as Nordic Ware Platinum cooking surface coating.

In some embodiments, substrate 22 is in the form of a sheet and the sheet is positioned on top of plate 28. Coating 24 is dispensed onto substrate 22 through tip 34. In some embodiments, the robotically controlled gel dispensing system applies coating 24 to sheet substrate 22 without any fixture or plate, such as, for example, plate 28 being applied to sheet substrate 22. It is envisioned that substrates 22 of various shapes and sizes can be coated using the robotically controlled gel dispensing system disclosed therein. That is, the use of the robotically controlled gel dispensing system for coating a substrate is not limited by the size, shape or form of the substrate.

In some embodiments, the robotically controlled gel dispensing system applies coating 24 to substrate 22 in various configurations, whether substrate 22 in in the form of an envelope, a sheet, or otherwise. In some embodiments, the robotically controlled gel dispensing system applies coating 24 to substrate 22 in rows. In some embodiments, the robotically controlled gel dispensing system applies coating 24 to substrate 22 in columns. In some embodiments, the robotically controlled gel dispensing system applies coating 24 to substrate 22 in selected shapes, such as, for example, squares, rectangles, etc. In some embodiments, the robotically controlled gel dispensing system applies coating 24 to substrate 22 in different colors. In some embodiments, the robotically controlled gel dispensing system applies coating 24 to substrate 22 in 3D shapes. In some embodiments, the robotically controlled gel dispensing system applies coating 24 to substrate 22 such that at least a portion of substrate 22 is not covered with coating 24 to facilitate handling of substrate 22 by a medical practitioner. In some embodiments, rows or other shapes may be deposited on a mesh. One may also envision a multiple colors by introducing multiple tip "printing" allowing for use guidance markings, numbering, and even a logo. Rows and other shapes, omitted regions, etc. may also be possible with this method thus allowing for an area on the device that is not slippery from the coating and aids in handling by the surgeon.

Figure 6A:
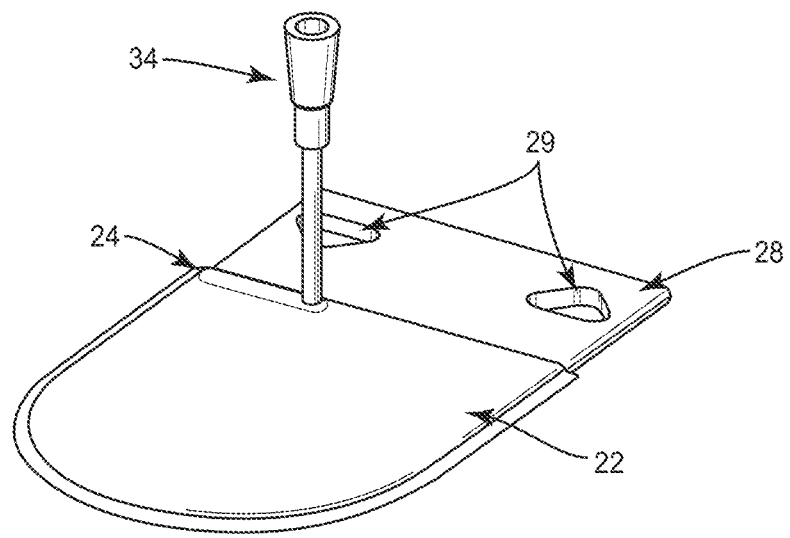
FIG. 6A is a perspective view showing one embodiment of making one embodiment of a component of the surgical system shown in FIG. 1, in accordance with the principles of the present disclosure.
Figure 6B:
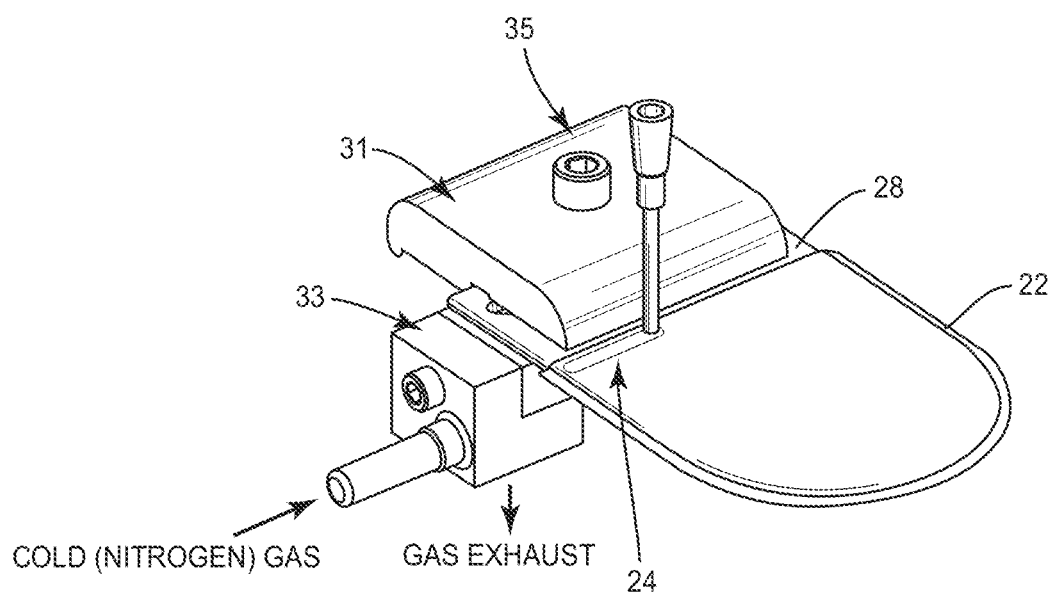
FIG. 6B is a perspective view showing one embodiment of making one embodiment of a component of the surgical system shown in FIG. 1, in accordance with the principles of the present disclosure.

In some embodiments, as shown in FIGS. 6A and 6B, system 15 is adapted to facilitate robotic handling and fixation. Plate 28 may include fixturing datur, such as, for example, apertures 29 that are configured for disposal of extensions (not shown) of a clamp block 31. In particular, the extensions of clamp block 31 are each positioned within one of apertures 29. Plate 28 is then sandwiched between clamp block 31 and a cooling block assembly 33 in any manner known in the art. Cooling block assembly 33 is configured to cool plate 28 via a refrigerated system to a temperature between −10 degrees Celsius and −20 degrees Celsius. In some embodiments, cooling block assembly 33 is configured to cool plate 28 via a refrigerated system to −15 degrees Celsius. In some embodiments, the refrigerated system uses liquid nitrogen boil-off gas that is applied directly to plate 28 and substrate 22. In some embodiments, clamp block 31 includes an engagement feature 35 that is configured for engagement with a component of system 15, such as, for example, a component of the robotically controlled gel dispensing system to apply a force to clamp block 31 to move clamp block 31 toward cooling block assembly 33 to directly engage surfaces of clamp block 31 and cooling block assembly 33 with plate 28 to fix plate 28 relative to clamp block 31 and cooling block assembly 33. In some embodiments, the component of the robotically controlled gel dispensing system that applies a force to clamp block 31 is an arm, such as, for example a hydraulic arm similar to that used with conventional drill presses. In some embodiments, engagement feature 35 can be variously connected with the component of the robotically controlled gel dispensing system that applies a force to clamp block 31, such as, for example, monolithic, integral connection, frictional engagement, threaded engagement, mutual grooves, screws, adhesive, nails, barbs, raised elements, spikes, clips, snaps, friction fittings, compressive fittings, expanding rivets, staples, fixation plates, key/keyslot, tongue in groove, dovetail, magnetic connection and/or posts. In some embodiments, apertures 29 may be variously shaped, such as, for example, oval, oblong, triangular, square, polygonal, irregular, uniform, non-uniform, offset, staggered, undulating, arcuate, variable and/or tapered.

Figure 7:
FIG. 7 is a perspective view showing one embodiment of making one embodiment of a component of the surgical system shown in FIG. 1, in accordance with the principles of the present disclosure.
Figure 8:
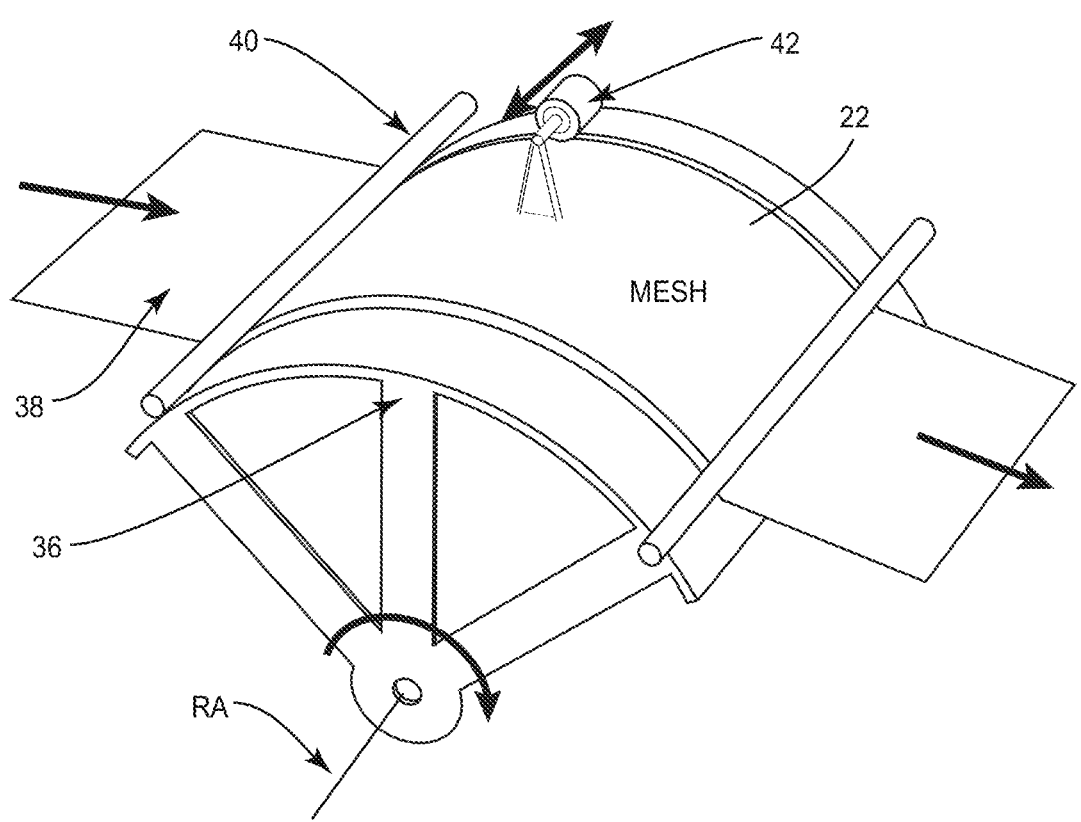
FIG. 8 is a perspective view showing one embodiment of making one embodiment of a component of the surgical system shown in FIG. 1, in accordance with the principles of the present disclosure.

In some embodiments, coating 24 is provided as a liquid or is sprayable such that coating 24 is sprayed onto substrate 22, as shown in FIGS. 7 and 8. As coating 24 is sprayed onto substrate 22, droplets and uneven concentration of coating 24 may form as coating 24 impacts substrate 22. In FIG. 7, the white plate is backing of the gray mesh such that the coating liquid wets out the mesh and backing plate. This avoids the formation of droplets that are evident outside the white (PTFE in the case) backing plate. In addition, such a coating eliminates the use of system antibiotics—the coating eludes the drug content in the target area of need. A non-systemic approach lowers the risk of over usage and subsequent resistant bacteria strains.

To ensure even wetting, substrate 22 is positioned on top of a plate 28 such that plate 28 contacts substrate 22 in areas where coating 24 will be deposited. Plate 28 allows for the even distribution of coating 24 over all of substrate 22 or in selected sections of substrate 22 and fills the interstitial spaces of substrate 22. This method is thus particularly useful when substrate 22 is in the form of a mesh. Plate 28 ensures capture of all of coating 24 rather than letting some of coating 24 pass through openings in substrate 22. In some embodiments, plate 28 is a flat plate. However, it is envisioned that plate 28 can have other forms, such as, for example, a drum or half pipe.

In some embodiments, for large substrates not the form of pouch that can be slipped over a fixture such as described above, in order to ensuring the single sheet stays in contact with the backing plate, it is convenient to stretch/place it over a cylindrical shape or substantially cylindrical. The "cylinder" may now be moved as one coordinate axis while a spray or fluid dispensing system traverses the orthogonal axis. In some embodiments, up to 10 times the concentration of the hemostatic agent (TXA) can be used thus allowing for coating with 10 times less initial volume of spray or deposition fluid. This comes with the above mentioned disadvantages when pre-wetting the device before implanting the device.

In one embodiment, shown in FIG. 8, a sheet, such as, for example, a polyimide liner 38 is positioned between a plate 36 and substrate 22. Hold down features, such as, for example, rods 40 are coupled to opposite ends of substrate 22 such that substrate 22 is positioned between rods 40 and liner 38. That is, liner 38 directly engages a first surface of substrate 22 and rods 40 directly engage an opposite second side of substrate 22 to couple substrate 22 to plate 36. System 15 includes an actuator or other device that is configured to rotate plate 36 while coating 24 is being deposited on substrate 22 or after coating 24 has been deposited on substrate such that the rotation of plate 36 evenly distributes coating 24 on substrate 22. As shown in FIG. 8, plate 36 has an arcuate configuration that facilitates distribution of coating 24 on substrate 22 as plate 36 rotates about a rotation axis RA. That is, as a spray head 42 sprays coating 24 onto substrate 22 and/or after head 42 spray coating 24 onto substrate 22, plate 36 rotates about axis RA to evenly distribute coating 24 along a surface of substrate. In some embodiments, plate 36 is cooled after coating 24 is deposited onto plate. In some embodiments, the backing plate may be cooled via a refrigerated system to a temperature between −10 C to −20 C with −15 C preferred target temp. In some embodiments, cooling is achieve by applying liquid nitrogen boil-off gas directly to both the fixture and device to be coated.

In some embodiments, coating 24 is selectively positioned on substrate 22 such that coating 24 is targeted to a location of blood loss in a patient when the anchorage device is implanted within the patient. In particular, coating 24 is selectively positioned on substrate 22 such that coating 24 is targeted to a location to prevent or reduce blood loss when the anchorage device is implanted within the patient. For example, once a location within the patient is identified where blood loss is likely to occur or is occurring, a medical practitioner may use anchorage device 20 wherein coating 24 positioned on substrate 22 such that coating 24 will be positioned adjacent to the location where blood loss is likely to occur or is occurring. As such, coating 24 will be able to effectively prevent, reduce or eliminate blood loss. In some embodiments, anchorage device 20 is delivered with coating 24 already applied to substrate 22. In some embodiments, anchorage device 22 is customizable. That is, the medical practitioner may be provided with a blank substrate, such as, for example, substrate 22 to which the medical practitioner can selectively apply coating 24. In particular, the medical practitioner can apply coating 24 to substrate 22 at a selected area of substrate 22 using one or more of the methods discussed herein for applying coating 24 to substrate 22, wherein the selected area(s) is an area of substrate 22 that will be positioned adjacent to the location within the patient where blood loss is occurring or likely to occur when anchorage device 20 is implanted within the patient.

In some embodiments, coating 24 is selectively positioned on substrate 22 to define a pattern on substrate 22. In some embodiments, the pattern includes vertical and/or horizontal stripes that each include coating 24. The stripes are spaced apart from one another by portions of substrate 22 that do not include coating 24. In some embodiments, the stripes are formed by applying a material, such as, for example, masking tape to substrate 22 in areas of substrate 22 where coating 24 is not desired. Substrate 22 is then sprayed, coated, dipped in, or washed with coating 24. The masking tape is then removed. It is envisioned that the process described herein about forming stripes may also be employed to apply coating 24 to substrate 22 to form any desired configuration. For example, the pattern can include a checkerboard pattern in which certain squares of the pattern each include coating 24 and other squares of the pattern are free of coating 24. In some embodiments, the pattern includes shapes that are arranged in rows and columns.

In some embodiments, substrate 22 is formed at least in part from hemostatic agent HA, as discussed herein. That is, substrate 22 is a hemostatic substrate that is made from hemostatic agent HA. In some embodiments, hemostatic substrate 22 is made only from hemostatic agent HA. In some embodiments, hemostatic agent HA does not include any coating, such as, for example, coating 24. In some embodiments, hemostatic agent HA includes a coating, such as, for example, coating 24. In some embodiments, coating 24 that is applied to hemostatic substrate 22 may include any of the coatings discussed herein. In some embodiments, coating 24 that is applied to hemostatic substrate 22 includes the API.

Coating 24 is applied to hemostatic substrate 22 to such that anchorage device 20 delivers hemostatic agent HA in combination with the API. In some embodiments, the API is applied directly to hemostatic substrate 22. That is, the API is not applied to hemostatic substrate 22 in a polymer, such as, for example, a polymer that includes the API. In some embodiments, the API is applied to hemostatic substrate 22 via a polymer, such as, for example, one of the polymers discussed herein, wherein the polymer includes the API and releases the API as the polymer degrades. In some embodiments, the API is applied to hemostatic substrate 22 via a polymer that includes also includes a hemostatic agent, such as, for example, one or more of the HAs. In some embodiments, the API is applied to hemostatic substrate 22 via a polymer that does not include the HA, such as, for example, a polymer that is free of the HA.

The API can include one or a combination of active pharmaceutical ingredients, such as, for example, anesthetics, antibiotics, anti-inflammatory agents, procoagulant agents, fibrosis-inhibiting agents, anti-scarring agents, antiseptics, leukotriene inhibitors/antagonists, cell growth inhibitors and mixtures thereof. In some embodiments, the API is an antibiotic. In some embodiments, the antibiotic is selected from the group consisting of rifampin and minocycline and mixtures thereof.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, l, and racemic isomers); and the methyl, ethyl, propyl, isopropyl, n-butyl, sec-butyl, t-butyl, esters of acetylsalicylic acid.

Examples of anesthetics include, but are not limited to, lidocaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocin, fentanyl, propoxyphene, hydromorphone, methadone, morphine, levorphanol, and hydrocodone. Local anesthetics have weak antibacterial properties and can play a dual role in the prevention of acute pain and infection.

Examples of antibacterial agents or antimicrobials include, but are not limited to, triclosan, chlorohexidine and other cationic biguanides, rifampin, minocycline (or other tetracycline derivatives), vancomycin, gentamycin; gendine; genlenol; genfoctol; clofoctol; cephalosporins and the like. Further antibacterial agents or antimicrobials include aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; hexachlorophene; cefamandole nafate; cefepime and its hydrochloride, sulfate, and phosphate salt; cefdinir and its sodium salt; ceftriaxone and its sodium salt; cefixime and its sodium salt; cetylpyridinium chloride; ofoxacin; linexolid; temafloxacin; fleroxacin; enoxacin; gemifloxacin; lomefloxacin; astreonam; tosufloxacin; clinafloxacin; cefpodoxime proxetil; chloroxylenol; methylene chloride, iodine and iodophores (povidone-iodine); nitrofurazone; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; α-terpineol; thymol; taurinamides; nitrofurantoin; silver-sulfadiazine; hexetidine; methenamine; aldehydes; azylic acid; silver; benzyl peroxide; alcohols; carboxylic acids; salts; nafcillin; ticarcillin and its disodium salt; sulbactam and its sodium salt; methylisothiazolone, moxifloxacin; amifloxacin; pefloxacin; nystatin; carbepenems; lipoic acids and its derivatives; beta-lactams antibiotics; monobactams; aminoglycosides; microlides; lincosamides; glycopeptides; tetracyclines; chloramphenicol; quinolones; fucidines; sulfonamides; macrolides; ciprofloxacin; ofloxacin; levofloxacins; teicoplanin; mupirocin; norfloxacin; sparfloxacin; ketolides; polyenes; azoles; penicillins; echinocandines; nalidixic acid; rifamycins; oxalines; streptogramins; lipopeptides; gatifloxacin; trovafloxacin mesylate; alatrofloxacin mesylate; trimethoprims; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin (and combinations thereof). In some embodiments the polymer may contain rifampin and another antimicrobial agent, such as, for example, an antimicrobial agent that is a tetracycline derivative. In some embodiments, the polymer contains a cephalosporin and another antimicrobial agent. In some embodiments, the polymer contains combinations including rifampin and minocycline, rifampin and gentamycin, and rifampin and minocycline.

When a mixture of two antibiotics is used, they generally present in a ratio ranging from about 10:1 to about 1:10. In some embodiments, a mixture of rifampin and minocycline are used. In those embodiments, a ratio of rifampin to minocycline ranges from about 5:2 to about 2:5. In other embodiments, the ratio of rifampin to minocycline is about 1:1.

Examples of antifungals include amphotericin B; pyrimethamine; flucytosine; caspofungin acetate; fluconazole; griseofulvin; terbinafine and its hydrochloride, sulfate, or phosphate salt; amorolfine; triazoles (Voriconazole); flutrimazole; cilofungin; LY303366 (echinocandines); pneumocandin; imidazoles; omoconazole; terconazole; fluconazole; amphotericin B, nystatin, natamycin, liposomal ampfericin B, liposomal nystatins; griseofulvin; BF-796; MTCH 24; BTG-137586; RMP-7/Amphotericin B; pradimicins; benanomicin; ambisome; ABLC; ABCD; Nikkomycin Z; flucytosine; SCH 56592; ER30346; UK 9746; UK 9751; T 8581; LY121019; ketoconazole; micronazole; clotrimazole; econazole; ciclopirox; naftifine; and itraconazole.

In some embodiments, active pharmaceutical ingredient API includes keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, aspirin, nicotinic acid, chemodeoxycholic acid, chlorambucil, paclitaxel, sirolimus, cyclosporins, 5-fluorouracil and the like.

In some embodiments, the API includes one or more ingredients that act as angiogenensis inhibitors or inhibit cell growth such as epidermal growth factor, PDGF, VEGF, FGF (fibroblast growth factor) and the like. These ingredients include anti-growth factor antibodies (neutrophilin-1), growth factor receptor-specific inhibitors such as endostatin and thalidomide. Examples of useful proteins include cell growth inhibitors such as epidermal growth factor.

Examples of anti-inflammatory compounds include, but are not limited to, anecortive acetate; tetrahydrocortisol, 4,9(11)-pregnadien-17α, 21-diol-3,20-dione and its -21-acetate salt; 111-epicortisol; 17α-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its -21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide.

Examples of leukotriene inhibitors/antagonists include, but are not limited to, leukotriene receptor antagonists such as acitazanolast, iralukast, montelukast, pranlukast, verlukast, zafirlukast, and zileuton.

In some embodiments, active pharmaceutical ingredient API includes sodium 2-mercaptoethane sulfonate ("MESNA"). MESNA has been shown to diminish myofibroblast formation in animal studies of capsular contracture with breast implants [Ajmal et al. (2003) Plast. Reconstr. Surg. 112:1455-1461] and may thus act as an anti-fibrosis agent.

Procoagulants include, but are not limited to, zeolites, thrombin, and coagulation factor concentrates.

In some embodiments, the amount of the API that is applied to hemostatic substrate 22 via coating 24 or otherwise ranges between about 0.3 to about 2.8 micrograms/cm$^2$. In other embodiments, the amount of the API that is applied to hemostatic substrate 22 via coating 24 or otherwise ranges between about 0.6 to about 1.4 micrograms/cm$^2$. In yet other embodiments, the amount of the API that is applied to hemostatic substrate 22 via coating 24 or otherwise ranges between about 0.85 to about 1.20 micrograms/cm$^2$. In yet further embodiments, the amount of the API that is applied to hemostatic substrate 22 via coating 24 or otherwise ranges between about 0.90 to about 1.10 micrograms/cm$^2$. In yet further embodiments, the amount of the API that is applied to hemostatic substrate 22 via coating 24 or otherwise ranges between about 50 to about 150 micrograms/cm$^2$. In yet further embodiments, the amount of the API that is applied to hemostatic substrate 22 via coating 24 or otherwise ranges between about 62 to about 140 micrograms/cm$^2$. In yet further embodiments, 62 micrograms/cm$^2$ of the API is applied to hemostatic substrate 22 via coating 24 or otherwise. In yet further embodiments, 140 micrograms/cm$^2$ of the API is applied to hemostatic substrate 22 via coating 24 or otherwise. In some embodiments, a first amount of the API is applied to hemostatic substrate 22 via coating 24 and a second amount is applied to hemostatic substrate 22 via a powder that is applied to substrate 22 after coating 24 is applied to substrate 22. For example, anchorage device 22 may be delivered to a medical practitioner with coating 24 being pre-applied to substrate 22 and including a standard amount of the API. The medical practitioner may then apply a powder, gel, slurry, solution, etc. of the API to the pre-applied coating 24 to add an additional amount of the API to anchorage device 20.

In some embodiments, the amount of the HA that is applied to hemostatic substrate 22 via coating 24 or otherwise ranges between about 0.3 to about 2.8 micrograms/cm$^2$. In other embodiments, the amount of the HA that is applied to hemostatic substrate 22 via coating 24 or otherwise ranges between about 0.6 to about 1.4 micrograms/cm$^2$. In yet other embodiments, the amount of the HA that is applied to hemostatic substrate 22 via coating 24 or otherwise ranges between about 0.85 to about 1.20 micrograms/cm$^2$. In yet further embodiments, the amount of the HA that is applied to hemostatic substrate 22 via coating 24 or otherwise ranges between about 0.90 to about 1.10 micrograms/cm$^2$. In yet further embodiments, the amount of the HA that is applied to hemostatic substrate 22 via coating 24 or otherwise ranges between about 50 to about 150 micrograms/cm$^2$. In yet further embodiments, the amount of the HA that is applied to hemostatic substrate 22 via coating 24 or otherwise ranges between about 62 to about 140 micrograms/cm$^2$. In yet further embodiments, 62 micrograms/cm$^2$ of the HA is applied to hemostatic substrate 22 via coating 24 or otherwise. In yet further embodiments, 140 micrograms/cm$^2$ of the HA is applied to hemostatic substrate 22 via coating 24 or otherwise. In some embodiments, a first amount of the HA is applied to hemostatic substrate 22 via coating 24 and a second amount is applied to hemostatic substrate 22 via a powder that is applied to substrate 22 after coating 24 is applied to substrate 22. For example, anchorage device 22 may be delivered to a medical practitioner with coating 24 being pre-applied to substrate 22 and including a standard amount of the HA. The medical practitioner may then apply a powder, gel, slurry, solution, etc. of the HA to the pre-applied coating 24 to add an additional amount of the HA to anchorage device 20.

In some embodiments, the amount of the HA and the API that is applied to hemostatic substrate 22 via coating 24 or otherwise ranges between about 0.3 to about 2.8 micrograms/cm$^2$. In other embodiments, the amount of the HA and the API that is applied to hemostatic substrate 22 via coating 24 or otherwise ranges between about 0.6 to about 1.4 micrograms/cm$^2$. In yet other embodiments, the amount of the HA and the API that is applied to hemostatic substrate 22 via coating 24 or otherwise ranges between about 0.85 to about 1.20 micrograms/cm$^2$. In yet further embodiments, the amount of the HA and the API that is applied to hemostatic substrate 22 via coating 24 or otherwise ranges between about 0.90 to about 1.10 micrograms/cm$^2$. In yet further embodiments, the amount of the HA and the API that is applied to hemostatic substrate 22 via coating 24 or otherwise ranges between about 50 to about 150 micrograms/cm$^2$. In yet further embodiments, the amount of the HA and the API that is applied to hemostatic substrate 22 via coating 24 or otherwise ranges between about 62 to about 140 micrograms/cm$^2$. In yet further embodiments, 62 micrograms/cm$^2$ of the HA and the API is applied to hemostatic substrate 22 via coating 24 or otherwise. In yet further embodiments, 140 micrograms/cm$^2$ of the HA and the API is applied to hemostatic substrate 22 via coating 24 or otherwise. In some embodiments, a first amount of the HA and the API is applied to hemostatic substrate 22 via coating 24 and a second amount of the HA and the API is applied to hemostatic substrate 22 via a powder that is applied to substrate 22 after coating 24 is applied to substrate 22. For example, anchorage device 22 may be delivered to a medical practitioner with coating 24 being pre-applied to substrate 22 and including a standard amount of the HA and the API. The medical practitioner may then apply a powder, gel, slurry, solution, etc. of the HA and the API to the pre-applied coating 24 to add an additional amount of the HA and the API to anchorage device 20.

In other embodiments, the API includes rifampin and minocycline and the amount of each of rifampin and minocycline that is applied to hemostatic substrate 22 ranges between about 0.6 to about 1.4 micrograms/cm$^2$. In yet other embodiments, the amount of each of rifampin and minocycline that is applied to hemostatic substrate 22 ranges between about 0.85 to about 1.20 micrograms/cm$^2$. In yet further embodiments, the amount of each of rifampin and minocycline that is applied to hemostatic substrate 22 ranges between about 0.90 to about 1.10 micrograms/cm$^2$. In some embodiments, a first amount of the rifampin and minocycline is applied to hemostatic substrate 22 via coating 24 and a second amount of the rifampin and minocycline is applied to hemostatic substrate 22 via a powder that is applied to substrate 22 after coating 24 is applied to substrate 22. For example, anchorage device 22 may be delivered to a medical practitioner with coating 24 being pre-applied to substrate 22 and including a standard amount of the rifampin and minocycline. The medical practitioner may then apply a powder, gel, slurry, solution, etc. of the rifampin and minocycline to the pre-applied coating 24 to add an additional amount of the rifampin and minocycline to anchorage device 20.

The API may include one or more of the active pharmaceutical ingredients discussed herein. The API may be incorporated into anchorage device 20 by applying the API directly to hemostatic substrate 22 or by applying the API to hemostatic substrate 22 via a polymer, such as, for example, one or more of the polymers discussed herein. Doses of the APIs discussed herein are known and the amounts of any single API to include in anchorage device 20 can readily be surmised. Any pharmaceutically acceptable form of APIs discussed herein can be employed in anchorage device 20, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate and the like.

In some embodiments, the API is applied directly to hemostatic substrate 22, as discussed herein. In some embodiments, the API may be applied to hemostatic substrate 22 by spraying active pharmaceutical ingredient API onto hemostatic substrate 22, coating all or a portion of hemostatic substrate 22 with the API, coating all or a portion of hemostatic substrate 22 with a material, such as, for example, one or more polymer that includes the API, washing hemostatic substrate 22 with the API, or printing the API on hemostatic substrate 22 with a printer, such as, for example a 3D printer. In some embodiments, the API is a material that forms hemostatic substrate 22. That is, hemostatic substrate 22 is made from the API and hemostatic agent HA is applied to hemostatic substrate 22.

In some embodiments, anchorage device 20 includes hemostatic substrate 22 wherein all or a portion of hemostatic substrate 22 is coated with a first coating that includes one or more of the HAs and a second coating that includes one or more of the APIs, wherein the first coating is free of any APIs other than the HAs and the second coating is free of any HAs. In some embodiments, the first coating is applied directly to substrate 22 such that the first coating covers all or a portion of substrate 22 and the second coating is applied over all or a portion of the first coating. In some embodiments, the second coating is applied directly to substrate 22 such that the second coating covers all or a portion of substrate 22 and the first coating is applied over all or a portion of the second coating. In some embodiments, anchorage device 20 includes multiple layers of the first coating and/or the second coating applied to substrate 22.

In some embodiments, coating 24 is selectively positioned on hemostatic substrate 22 such that coating 24 is targeted to a location to treat at least one condition when anchorage device 20 is implanted within the patient. For example, once a location within the patient is identified that has a certain condition, such as, for example, infection, scarring and/or infection, a medical practitioner may use anchorage device 20 with coating 24 positioned on hemostatic substrate 22 such that coating 24 will be positioned adjacent to the location having the condition when anchorage device 20 is implanted within the patient. As such, coating 24 will be able to effectively treat the condition by, for example, providing pain relief, inhibiting scarring or fibrosis and/or inhibiting bacterial growth.

The polymer discussed herein, such as, for example, the polymer of coating 24 that contains the HA and/or the API is selected from the group consisting of polylactic acid, polyglycolic acid, poly(L-lactide), poly(D,L-lactide) polyglycolic acid[polyglycolide], poly(L-lactide-co-D,L-lactide), poly(L-lactide-co-glycolide), poly(D, L-lactide-co-glycolide), poly(glycolide-co-trimethylene carbonate), poly (D,L-lactide-co-caprolactone), poly(glycolide-co-caprolactone), polyethylene oxide, polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, copolymers of polyhydroxybutyrate, poly (phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose. In some embodiments, the polymer may include combinations, blends or mixtures of the polymers discussed herein. In some embodiments, the polymer includes the HA and the API dispersed therein. In some embodiments, the HA and the API are uniformly dispersed in the polymer.

In some embodiments, the polymer is a polyarylate. In some embodiments, the polymer is a tyrosine-derived polyarylate. In some embodiments, the tyrosine-derived polyarylate is p(DTE co X % DT succinate), where X is about 10% to about 30%. In some embodiments, the tyrosine-derived polyarylate is p(DTE co X % DT succinate), where X ranges from about 26.5% to about 28.5%. In some embodiments, the tyrosine-derived polyarylate is p(DTE co X % DT succinate), where X is about 27.5%. In some embodiments, the polymer is P22-27.5 DT.

As used herein, DTE is the diphenol monomer desaminotyrosyl-tyrosine ethyl ester; DTBn is the diphenol monomer desaminotyrosyl-tyrosine benzyl ester; DT is the corresponding free acid form, namely desaminotyrosyl-tyrosine. BTE is the diphenol monomer 4-hydroxy benzoic acid-tyrosyl ethyl ester; BT is the corresponding free acid form, namely 4-hydroxy benzoic acid-tyrosine.

P22-XX is a polyarylate copolymer produced by condensation of DTE and DTBn with succinic acid followed by removal of benzyl group. P22-10, P22-15, P22-20, P22-XX, etc., represents copolymers different percentage of DT (i.e., 10, 15, 20 and % DT, etc.) In some embodiments, the polymer is produced by condensation of DTBn with succinic acid followed by removal of benzyl group. This polymer is represented as P02-100.

In some embodiments, the polymer includes one or more polyarylates that are copolymers of desaminotyrosyl-tyrosine (DT) and an desaminotyrosyl-tyrosyl ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of polyarylates are the same as the foregoing but the desaminotyrosyl moiety is replaced by a 4-hydroxybenzoyl moiety. In some embodiments, the DT or BT contents include those copolymers with from about 1% to about 30%, from about 5% to about 30% from about 10 to about 30% DT or BT. In some embodiments, the diacids (used informing the polyarylates) include succinate, glutarate and glycolic acid.

In some embodiments, the polymer includes one or more biodegradable, resorbable polyarylates and polycarbonates. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate, DT PEG ester succinate, DTMB P(Desaminotyrsoyl tyrosine methylparaben ester-glutarate), and DTPP P(Desaminotyrsoyl tyrosine propylparaben ester-glutarate).

In some embodiments, the polymer is one more polymers from the DTE-DT succinate family of polymers, e.g., the P22-xx family of polymers having from 0-50%, 5-50%, 5-40%, 1-30% or 10-30% DT, including but not limited to, about 1, 2, 5, 10, 15, 20, 25, 27.5, 30, 35, 40%, 45% and 50% DT. In some embodiments, the polymer is P22-27.5 DT.

In some embodiments, the polymer has diphenol monomer units that are copolymerized with an appropriate chemical moiety to form a polyarylate, a polycarbonate, a polyiminocarbonate, a polyphosphonate or any other polymer.

In some embodiments, the polymer is tyrosine-based polyarylate. In some embodiments, the polymer includes blends and copolymers with polyalkylene oxides, including polyethylene glycol (PEG).

In some embodiments, the polymer can have from 0.1-99.9% PEG diacid to promote the degradation process. In some embodiments, the polymer includes blends of polyarylates or other biodegradable polymers with polyarylates.

The polymer is configured to release the HA and/or the API over time, as discussed herein. In some embodiments, the polymer is configured to release the HA and/or the API over a time period ranging from about 1 hour to about 168 hours. In some embodiments, the polymer is configured to release the HA and/or the API over a time period ranging from 1 hour to 72 hours. In some embodiments, the polymer is configured to release the HA and/or the API over a time period ranging from 1 hour to 24 hours.

In some embodiments, the polymer is configured to release the HA and/or the API over time in an area surrounding or adjacent to anchorage device 20 (such as, for example, within the device "pocket" or within 3 inches in all dimensions). In some embodiments, the polymer is configured to release the HA and/or the API for up to 30 hours. In some embodiments, the polymer is configured to release between about 40% and about 100% of the HA and/or the API over a period of at least about 30 hours. In some embodiments, the polymer is configured to release 60% and about 100% of the HA and/or the API over a period of at least about 30 hours. In some embodiments, the polymer is configured to release between about 65% and about 100% of the HA and/or the API over a period of at least about 36 hours. In some embodiments, the polymer is configured to release 80% and about 100% of the HA and/or the API over a period of at least about 36 hours. In some embodiments, the polymer is configured to release between about 60% and about 100% of the HA and/or the API over a period of at least about 48 hours. In some embodiments, the polymer is configured to release 80% and about 100% of the HA and/or the API over a period of at least about 48 hours. In some embodiments, the polymer is configured to release between about 60% and about 100% of the HA and/or the API over a period of at least about 60 hours. In some embodiments, the polymer is configured to release 80% and about 100% of the HA and/or the API over a period of at least about 60 hours. In some embodiments, the polymer is configured to release 80% and about 100% of the HA and/or the API within 48 hours. In some embodiments, the polymer is configured to release 80% and about 100% of the HA and/or the API within 24 hours.

In some embodiments, the polymer is configured to release no more than 60% of the HA and/or the API within 24 hours. In some embodiments, the polymer is configured to release no more than 90% of the HA and/or the API after 60 hours. In some embodiments, the polymer is configured to release no more than 50% of the HA and/or the API within 12 hours. In some embodiments, the polymer is configured to release between about 40% and about 90% of the HA and/or the API between 12 and 24 hours. In some embodiments, the polymer is configured to release between about 60% and about 100% of the HA and/or the API between 24 and 36 hours. In some embodiments, the polymer is configured to release between about 65% and about 100% of the HA and/or the API between 36 and 48 hours. In some embodiments, the polymer is configured to release between about 70% and about 100% of the HA and/or the API between 48 and 60 hours.

Substrate 22 may be coated with single or multiple coating layers of coating 24, depending on, for example, the amount of the HA and/or the API to be delivered and desired release rate. Each layer of coating 24 may contain the same or different amounts of the HA and/or the API. For example, a first layer of coating 24 may contain the HA and/or the API, while the second layer of coating 24 contains either no HA or API or a lower concentration of the HA and/or the API. As another example, a first layer of coating 24 may comprise the HA and/or the API in a first polymer, while the second layer of coating 24 comprises the HA and/or the API in a second polymer that is different than the first polymer.

Figure 3:
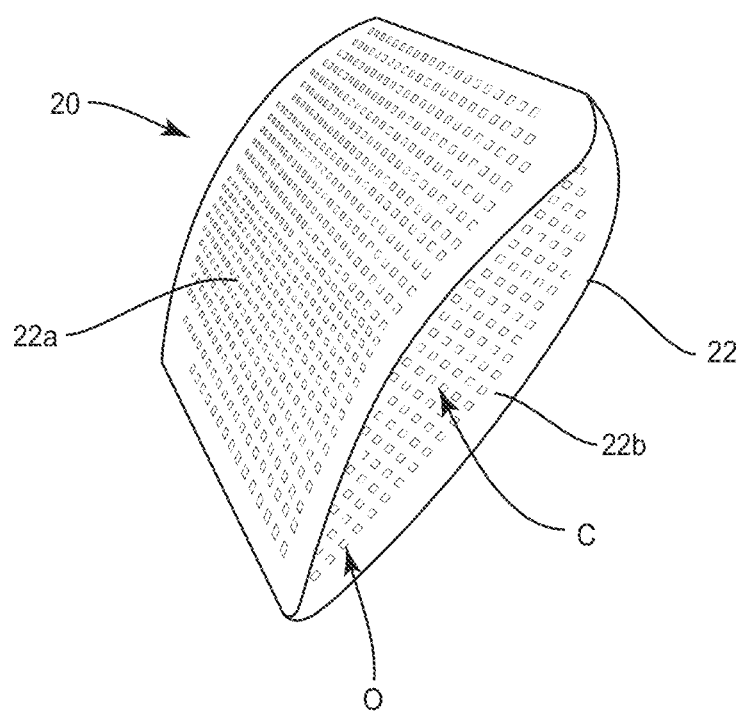
FIG. 3 is a perspective view of one embodiment of a component of the surgical system shown in FIG. 1, in accordance with the principles of the present disclosure.
Figure 4:
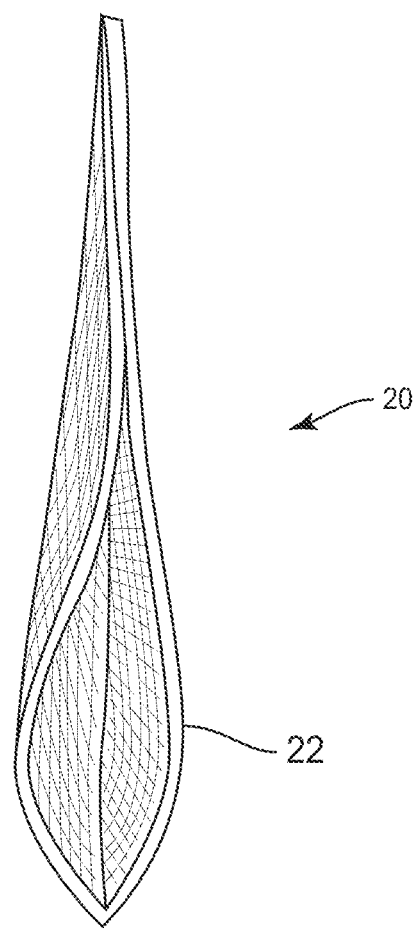
FIG. 4 is a perspective view of one embodiment of a component of the surgical system shown in FIG. 1, in accordance with the principles of the present disclosure.

In some embodiments, shown in FIGS. 3 and 4, substrate 22 is a pocket or envelope in which medical device 25 can be at least partially disposed. That is, substrate 22 is a pouch, bag, covering, shell, or receptacle. For example, substrate 22 can include a first piece 22a and a second piece 22b that is joined with first piece 22a. First and second pieces 22a, 22b are joined to form the pocket or envelope. In some embodiments, first and second pieces 22a, 22b are joined along three sides of the pocket or envelope to form a cavity C. First and second pieces 22a, 22b are not joined at a fourth side of the pocket or envelope to define opening O such that medical device 25 can be inserted through opening O and into cavity C to enclose, encase or surround all or a portion of medical device 25 within cavity C. In some embodiments, first and second pieces 22a, 22b are joined with one another along three sides of the pocket or envelope by heat, ultrasonically, bonding, knitting, or adhesive. In some embodiment, the pocket or envelope is monolithically formed by molding the pocket or envelope or producing the pocket or envelope by 3D printing, for example. In some embodiments, anchorage device 20 is pre-formed to provide cavity C with a selected size and shape. In some embodiments, the selected size and shape of cavity conforms to the size and shape of medical device 25. In some embodiments, the selected size and shape of cavity conforms to the size and shape of medical device 25 and the size and shape of an insert of a package, as discussed herein. That is, the insert and medical device 25 have the same size and shape so that the insert can be inserted into cavity C while anchorage device 20 is packaged and medical device 25 can be inserted into cavity C when anchorage device 20 is unpackaged, as discussed herein. In some embodiments, opening O is configured to have a selected size and shape that allows the insert and medical device 25 to be inserted through opening O and into cavity C. In some embodiments, substrate 22 is made from a material or includes a reinforcing material (e.g., stitching) or other structure around opening O that allows opening O to maintain the selected size and shape of opening O. That is, opening O will not collapse without any structure between pieces 22a, 22b or any force that spaces piece 22a away from piece 22b. This allows opening O to maintain the selected size and shape when the insert or medical device 25 is not positioned in cavity C or opening O. In some embodiments, substrate 22 is made from a material that causes opening O to collapse from the selected size and shape of opening O to a size and shape that is smaller than the selected size and shape of opening O. That is, opening O will collapse without any structure between pieces 22a, 22b or a force that spaces piece 22a away from piece 22b. As such, opening O will collapse when the insert or medical device 25 are not positioned in cavity C or opening O.

In some embodiments, first and second pieces 22a, 22b are portions of a single sheet that is bent to produce a fold at one end of the pocket or envelope. First and second pieces 22a, 22b are joined along sides of the pocket or envelope that extend transverse to the fold such that the fold and the sides of the pocket or envelope do not have any openings. First and second pieces 22a, 22b are not joined at an end of the pocket or envelope opposite the fold to define an opening at the end such that medical device 25 can be inserted through the opening and into a cavity defined by inner surfaces of first and second pieces 22a, 22b.

In some embodiments, first and second pieces 22a, 22b each include a mesh. In some embodiments, first piece 22a includes a mesh including pores having a first size and second piece 22b includes a mesh including pores having a second size, wherein the first size is different than the first size. In some embodiments, the first size is greater than the second size. In some embodiments, the first size is less than the second size. In some embodiments, first and second pieces 22a, 22b each include a thin walled structure that does not have any pores or apertures. In some embodiments one of first and second pieces 22a, 22b includes a mesh and the other one of first and second pieces 22a, 22b includes a thin walled structure that does not have any pores or apertures.

In some embodiments, first and second pieces 22a, 22b are formed from the same material. In some embodiments one of first and second pieces 22a, 22b is formed from a first material, such as, for example, one or more of the materials discussed herein, and the other one of first and second pieces 22a, 22b is made from a second material, such as, for example, one or more of the materials discussed herein, wherein the second material is different than the first material. For example, first piece 22a may be formed from a biodegradable and/or bioresorbable material and second piece 22b may be formed from a non-biodegradable and/or non-bioresorbable material, or vice versa. In some embodiments, first and second pieces 22a, 22b are each formed from a biodegradable and/or bioresorbable material, wherein the biodegradable and/or bioresorbable materials degrade and/or resorb at the same rate. In some embodiments, first and second pieces 22a, 22b are formed from different biodegradable and/or bioresorbable materials, wherein one of the biodegradable and/or bioresorbable materials degrades and/or resorbs more quickly than the other biodegradable and/or bioresorbable material.

In some embodiments, first and second pieces 22a, 22b each include a single layer of material, such as, for example, one or more of the materials discussed herein. In some embodiments, at least one of first and second pieces 22a, 22b includes multiple layers. In some embodiments, the multiple layers include more than one layer of a mesh. In some embodiments, the multiple layers include more than one layer of a thin walled structure that does not have any pores or apertures. In some embodiments, the multiple layers include one or more layer of a mesh and one or more layer of a thin walled structure that does not have any pores or apertures. In some embodiments, the multiple layers include one or more layer of a mesh and one or more layer of a thin walled structure, wherein one of the layers of mesh is positioned between two layers of the thin walled structure. In some embodiments, the multiple layers include one or more layer of a mesh and one or more layer of a thin walled structure that does not have any pores or apertures, wherein one of the layers of thin walled structure is positioned between two layers of the mesh.

In embodiments discussed herein wherein anchorage device 20 is a pocket or envelope, a first coating 24 can be applied to first piece 22a and a second coating 24 can be applied to second piece 22b. In some embodiments, the first and second coatings 24 are different. In some embodiments, the first and second coatings 24 release the HA and/or the API at different rates and/or over different lengths of time. In some embodiments, the first coating 24 includes a first amount of the HA and/or the API and the second coating 24 includes a second amount of the HA and/or the API, the first amount being different than the second amount. In some embodiments, the first and second coatings 24 are the same.

In some embodiments, anchorage device 20 includes a hydrophilic component, such as, for example, PEG and a crosslinking agent that is applied to substrate 22. The hydrophilic component and the crosslinking agent form a hydrogel that absorbs blood and reduces bleeding when in contact with blood or tissue fluid. In some embodiments, the hydrophilic component and the crosslinking agent are sprayed directly onto substrate 22. In some embodiments, the hydrophilic component and the crosslinking agent are provided in a polymer, such as, for example, one or more of the polymers discussed herein, and the polymer is applied directly onto substrate 22. In some embodiments, the hydrophilic component and the crosslinking agent are provided in a patch, such as, for example, the Veriset™ hemostatic patch available from Medtronic, Inc., and the patch is applied directly onto substrate 22. In some embodiments, the patch comprises a plurality of layers. For example, a first layer of the patch can include a hemostatic agent, such as, for example, oxidized regenerated cellulose and/or one or more of the hemostatic agents discussed herein. A second layer of the patch can include a crosslinking agent, such as, for example, trilysine and/or one or more of the crosslinking agents discussed herein. A third layer of the patch can include a hydrophilic agent, such as, for example, PEG and/or one or more of the hydrophilic agents discussed herein. The second layer of the patch is positioned between the first and third layers of the patch.

In some embodiments, the hydrophilic component comprises thermogelling hydrogels, PEG-PLGA copolymers, PEG-Poly(N-isopropyl acrylamide), Pluronic (PEO-PPO-PEO triblock), PEG-PCL polymers, PEG-based amphiphilic copolymers modified by anionic weak polyelectrolytes, (such as polyacrylic acid, polyglutamic acid) and polymers containing sulfonamide groups), PEG-based amphiphilic copolymers modified by cationic weak polyelectrolytes (such as poly (2-vinyl pyridine), Poly(beta-amino esters), poly (2-(dimethylamino)ethyl methacrylate), multiarm PEG derivatives such as those available from JenKem technology, multiarmed block and graft PLA copolymers with PEG, PEG with stereo complexed poly(lactide), acrylated polymers (such as Polyvinylalcohol, dextran, Polyvinylpyrollidone, chitosan, alginate, hyaluronic acid), and combinations thereof. In some embodiments, the crosslinking agent comprises one or more agents that induce polymerization of vinyl groups using various initiators, light or redox reactions, or by reactions such as Schiff base formation, Michael type additions, peptide ligation, clock chemistry of functional groups present; one or more agents that induce crosslinking by enzymatic reaction (transglutaminase mediated reaction between carboxamide and amine on proteins), stereo-complexation, metal chelation (alginates using calciumCal2), thermogelation, self-assembly (formation of super helices from protein chains) inclusion complexation (using cyclodextrin); and combinations thereof.

In some embodiments, an anchorage device, such as, for example, anchorage device 20 and a medical device, such as, for example, medical device 25 are implanted into a body of a patient. The anchorage device releases a hemostatic agent or active pharmaceutical ingredient, such as, for example, the HA and/or the API, to reduce or prevent bleeding within the patient or treat one of the conditions as discussed herein. In some embodiments, anchorage device 20 is implanted within the patient without medical device 25 and medical device 25 is coupled to or inserted into anchorage device 20 after anchorage device 20 is implanted. In some embodiments, medical device 25 is coupled to or inserted into anchorage device 20 before anchorage device 20 is implanted within the patient and anchorage device 20 and medical device 25 are implanted within the patient together.

In some embodiments, medical device 25 is removed from the patient after the treatment is completed. In some embodiments, anchorage device 20 remains implanted within the patient after medical device 25 is removed. In some embodiments, anchorage device 20 is removed from the patient after medical device 25 is removed. To remove anchorage device 20, tissue that is ingrown within substrate 22 of anchorage device 22 can be cut or otherwise detached from substrate 22. In some embodiments, a portion of anchorage device 20 may not be removable from the tissue and will remain implanted within the patient.

In some embodiments, the method includes making a customized anchorage device, wherein a hemostatic agent and/or active pharmaceutical ingredient is selectively applied to the anchorage device to position the hemostatic agent or active pharmaceutical ingredient such that the hemostatic agent is targeted to a location of blood loss in a patient when the anchorage device is implanted within the patient or such that active pharmaceutical ingredient is targeted to a location to treat at least one condition when the anchorage device is implanted within the patient. As such, the method includes identifying a location within the patient that has a certain condition, such as, for example, infection, scarring and/or infection, or a location where blood lose is occurring or is likely to occur. The medical practitioner than may select a portion or portions of the substrate to which hemostatic agent and/or active pharmaceutical ingredient should be applied so that the hemostatic agent or active pharmaceutical ingredient is positioned at or adjacent to the location within the patient when the anchorage device is implanted within the patient. In some embodiments, the method further includes applying the hemostatic agent and/or active pharmaceutical ingredient to the substrate at the selected portion or portions of the substrate. For example, in one embodiment, the method includes loading data into a computer regarding the selected portion or portions of the substrate and using a 3D printer that is connected to the computer to print the hemostatic agent and/or active pharmaceutical ingredient onto the selected portion or portions of the substrate. It is envisioned that the medical practitioner may also select the amount of the hemostatic agent and/or active pharmaceutical ingredient that is applied to the portion or portions of the substrate. For example, the medical practitioner can choose to apply more of the hemostatic agent and/or active pharmaceutical ingredient to one portion of the substrate than another portion of the substrate. This information can be input into the computer such that the 3D printer prints the selected amounts of the hemostatic agent and/or active pharmaceutical ingredient on the portion or portions of the substrate. In some embodiments, the medical practitioner may choose to apply more of the hemostatic agent and/or active pharmaceutical ingredient on one portion of the substrate than another portion of the substrate or the same amount of the hemostatic agent and/or active pharmaceutical ingredient on each portion of the substrate. It is envisioned that the anchorage device with the hemostatic agent and/or active pharmaceutical ingredient applied to the selected portion or portions of the substrate in the selected amounts can be made in a manufacturing facility, in a hospital, or in an operating room. In some embodiments, the process of making the anchorage device may include starting with a blank substrate and then applying the hemostatic agent and/or active pharmaceutical ingredient to the blank substrate in the manner discussed above. In some embodiments, the process of making the anchorage device includes forming the substrate and applying the hemostatic agent and/or active pharmaceutical ingredient to the substrate. In some embodiments, the process of making the anchorage device includes forming the substrate with the hemostatic agent and/or active pharmaceutical ingredient applied to the substrate simultaneously. For example, a medical practitioner can input into a computer the type of substrate desired (size, shape, material, etc.) the portions of the substrate that should include the hemostatic agent and/or active pharmaceutical ingredient, and the amounts of the hemostatic agent and/or active pharmaceutical ingredient to be included in each of the portions. A 3D printer that is connected to the computer can then print the substrate with the hemostatic agent and/or active pharmaceutical ingredient on the substrate at the selected portions and in the selected amounts.

Figure 9:
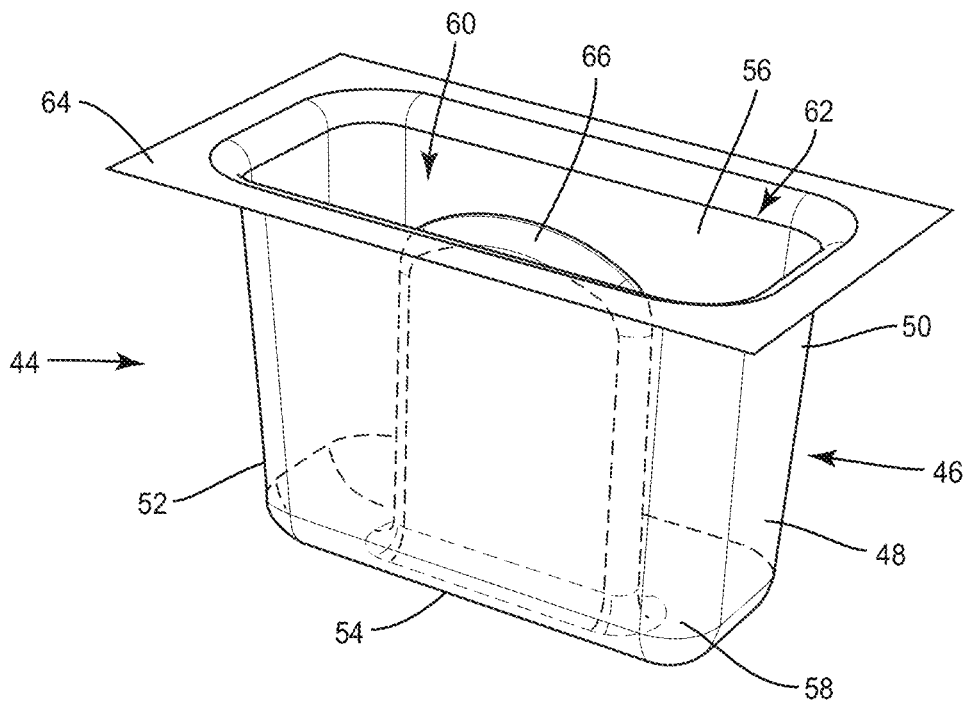
FIG. 9 is a perspective view of one embodiment of a component of the surgical system shown in FIG. 1, in accordance with the principles of the present disclosure.
Figure 10:
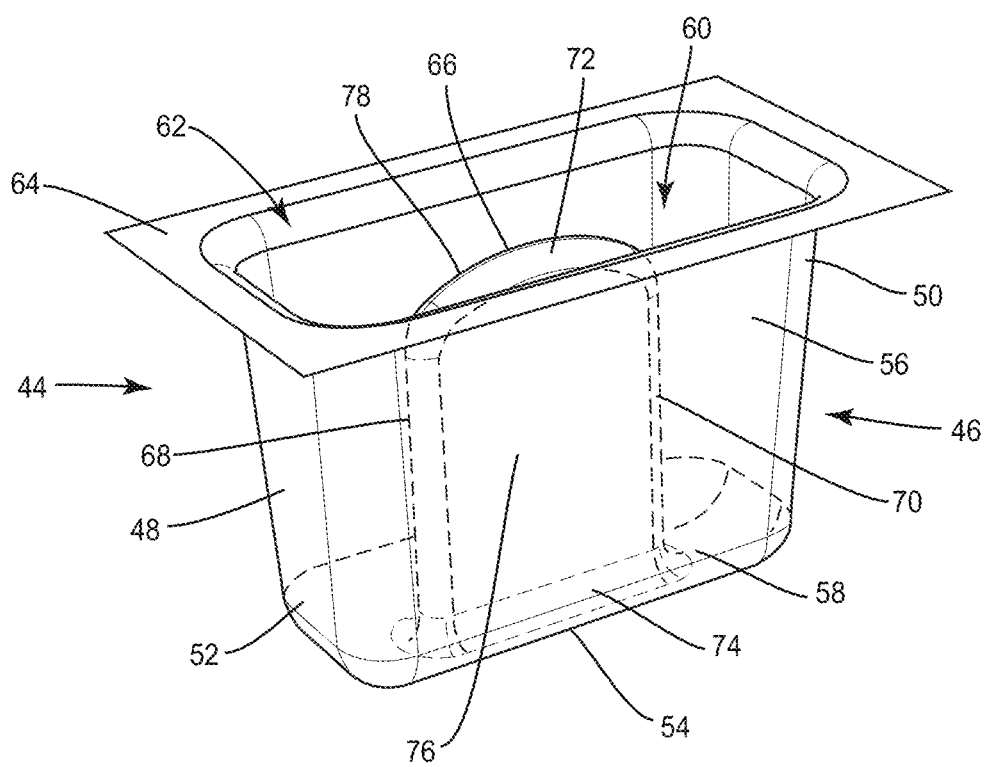
FIG. 10 is a perspective view of one embodiment of a component of the surgical system shown in FIG. 1, in accordance with the principles of the present disclosure.
Figure 11:
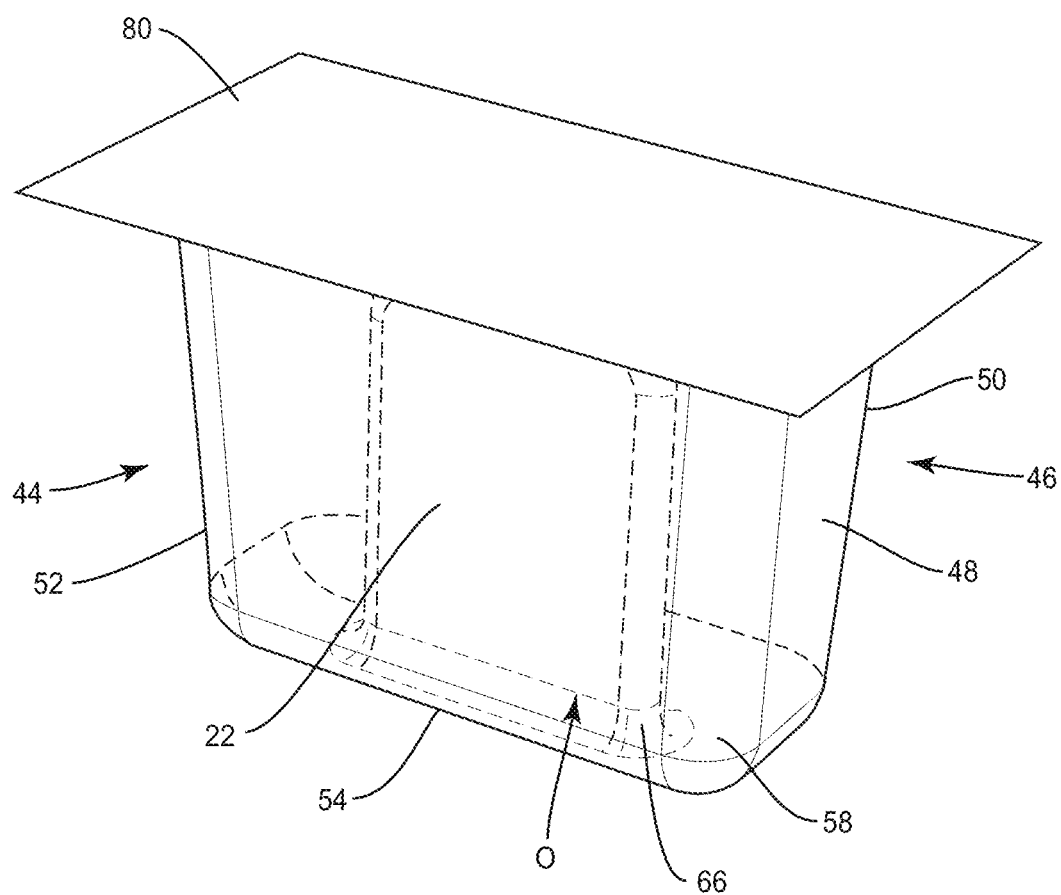
FIG. 11 is a perspective view of one embodiment of a component of the surgical system shown in FIG. 1 packaged within another component of the surgical system shown in FIG. 1, in accordance with the principles of the present disclosure.

In some embodiments, system 15 include a package 44, shown in FIGS. 9-11, configured to house anchorage device 20 as anchorage device 20 is being transported from a manufacturer to a user, such as, for example, a medical practitioner. Package 44 includes a body 46 having a side wall 48. Wall 48 includes a top end 50 and an opposite bottom end 52. Body 46 comprises a bottom wall 54 coupled to end 52. An inner surface 56 of wall 56 and an inner surface 58 of wall 54 define a cavity 60. End 50 defines an opening 62 that is in communication with cavity 60. In some embodiments, body 46 includes a flange 64 extending outwardly from end 50. Opening 62 extends through flange 64. In some embodiments, all or a portion of body 46 is opaque to prevent light from moving through wall 48 and/or wall 54 to maintain sterility within cavity 60. In some embodiments, all or a portion of body 46 is transparent to allow medical device 25 to be viewed through wall 48 and/or wall 54 when medical device 25 is positioned within cavity 60.

In some embodiments, materials for vacuum thermal forming include Acrylonitrile butadiene styrene (ABS), Polychlorotrifluoroethylene (PCTFE), polyvinyl chloride (PVC), Polyvinylidene chloride (PVDC), Cyclic olefin copolymers (COC) or polymers (COP). Packaging final thickness may range from 0.005" to 0.020" or so depending on stiffness of the chosen plastic and necessary moisture blocking. The materials may be blow molded or cold formed. However, vacuum thermal forming is likely the most economical.

Package 44 further includes an insert 66 extending from wall 54 such that insert 66 is positioned in cavity 60. Insert 66 has a size and shape defined by a first side wall 68 and an opposite second side wall 70. Walls 68, 70 each extend from a top wall 72 of insert 66 to an opposite bottom wall 74 of insert 66. In some embodiments, the wall 72 is convexly curved from wall 68 to wall 70. In some embodiments, the wall 68 extends parallel to wall 70 from wall 72 to wall 74. In some embodiments, insert 66 includes a front wall 76 and an opposite back wall 78 that each extend from wall 72 to wall 74 and from wall 68 to wall 70. In some embodiments, wall 76 extends parallel to wall 78 from wall 72 to wall 74.

In embodiments wherein anchorage device 20 is an envelope, as discussed herein, anchorage device can be inserted into package 44 by inserting anchorage device 20 into cavity 60 such that that insert 66 is positioned within cavity C. That is, anchorage device 20 is moved relative to package 44 such that insert 66 moves through opening O and into cavity C. In some embodiments, insert 66 forms a close fit with anchorage device 20 such that an inner surface of anchorage device that defines cavity C directly engages an outer surface of insert 66. In some embodiments, the outer surface of insert 66 is smooth and/or even to prevent tearing or otherwise damaging anchorage device 20. In some embodiments, the outer surface of insert 66 is rough and/or textured to facilitate gripping of insert 66 with anchorage device 20. In some embodiments, package 44 includes a lid, such as, for example, a cover 80 that is attached to flange 64 such that cover 80 completely covers opening 62, as shown in FIG. 11. In some embodiments, cover 80 is coupled to flange 64 via adhesive. In some embodiments, cover 80 is sealed or bonded to flange 64 using heat sealing. In some embodiments, cover 80 cannot be removed from body 46 without damaging and/or breaking cover 80 to prevent cover 80 from being reattached to body 46.

In some embodiments, all or a portion of package 44 is made from polyethylene terephythalate (PET). In some embodiments, package 44 comprises one or more layers having an oxygen barrier material. In some embodiments, the oxygen barrier material is present in the container in an amount between about 0.5 wt. % and about 5.0 wt. % of the container. In some embodiments, the oxygen barrier material is present in the container in an amount about 2.0 wt. % of the container. In some embodiments, the oxygen barrier is a passive barrier and is unreactive with oxygen. In some embodiments, the oxygen barrier is an oxygen scavenger and is reactive with oxygen to capture the oxygen. In some embodiments, the oxygen scavenger includes one or more oxygen barrier, such as, for example, one or more polymers, metals, compatibilizers, catalysts, and/or fatty acid salts.

Figure 12:
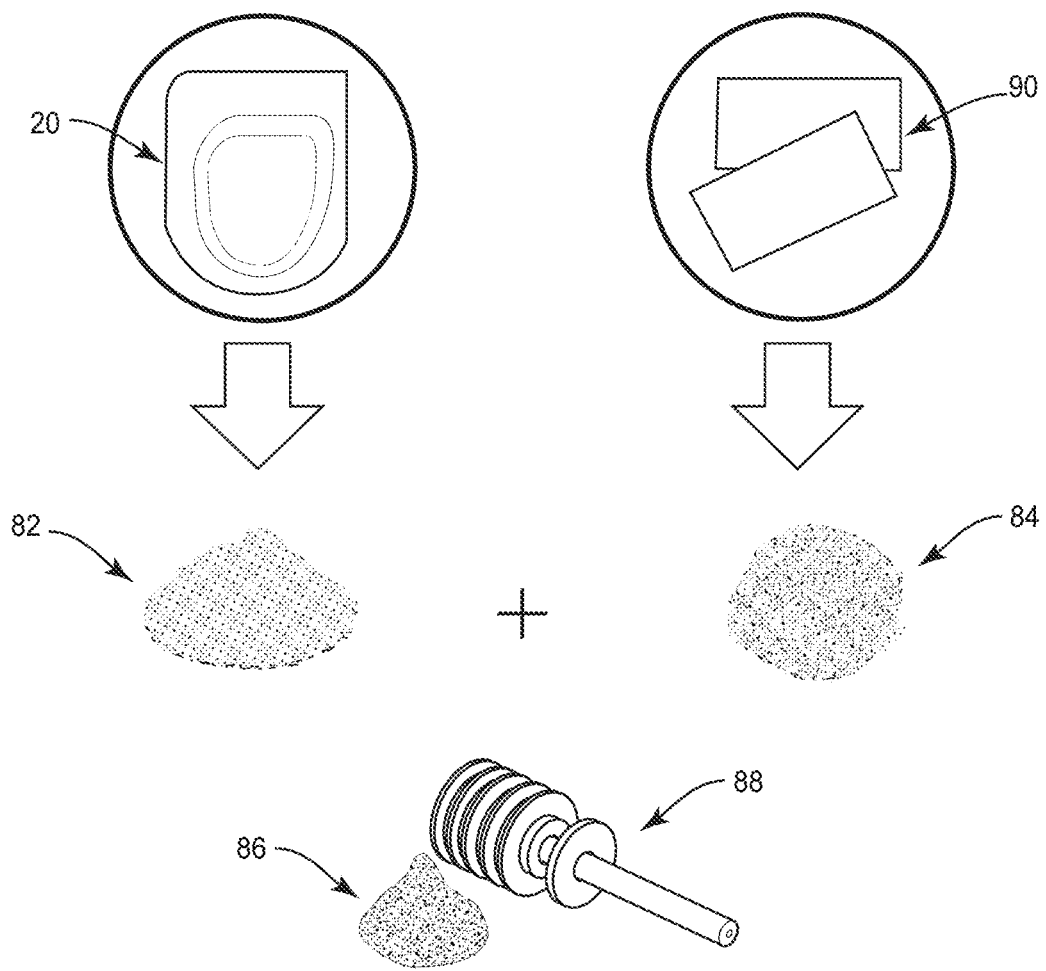
FIG. 12 is a perspective view showing one embodiment of making one embodiment of a component of a surgical system in accordance with the principles of the present disclosure.
Figure 13:
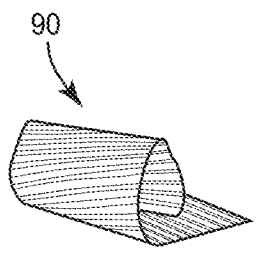
FIG. 13 is a perspective view of one embodiment of a component of the surgical system shown in FIG. 12, in accordance with the principles of the present disclosure.
Figure 14:
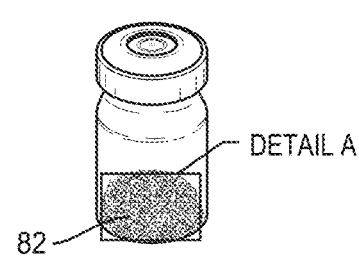
FIG. 14 is a perspective view of one embodiment of a component of the surgical system shown in FIG. 12, in accordance with the principles of the present disclosure.
Figure 15:
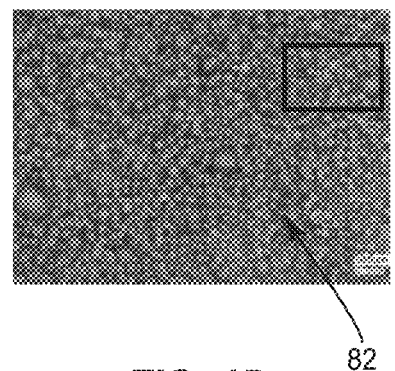
FIG. 15 is a perspective view of one embodiment of a component of the surgical system shown in FIG. 12, in accordance with the principles of the present disclosure, taken at detail A in FIG. 14.

In some embodiments, system 15 includes a powder that includes one or more of the HAs and one or more of the APIs, as discussed herein. In particular, the one or more HAs are included in a first powder 82 and the one or more APIs are included in a second powder 84. First and second powders 82, 84 are combined to create a third powder 86, as shown in FIG. 12. In some embodiments, the ratios of powder can range from 9:1 through 1:9, with the preferred ratio about 1:1.

Figure 16:
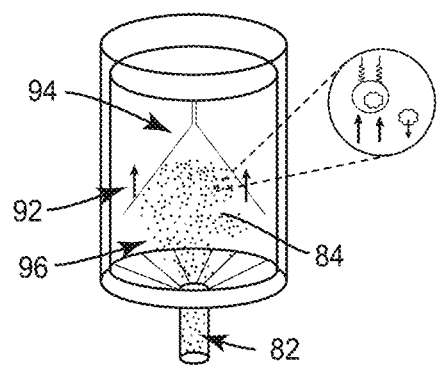
FIG. 16 is a perspective view of one embodiment of a component of the surgical system shown in FIG. 12, in accordance with the principles of the present disclosure.
Figure 17:
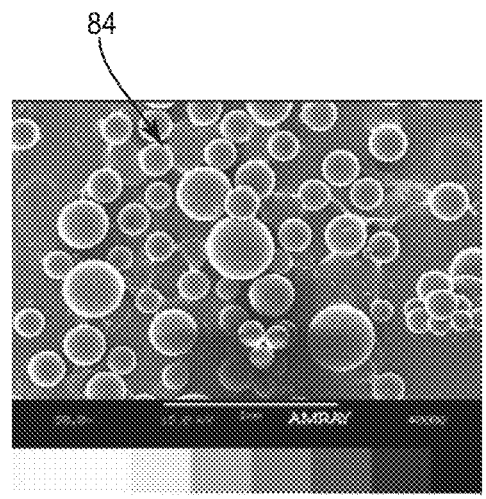
FIG. 17 is a perspective view of one embodiment of a component of the surgical system shown in FIG. 12, in accordance with the principles of the present disclosure.
Figure 18:
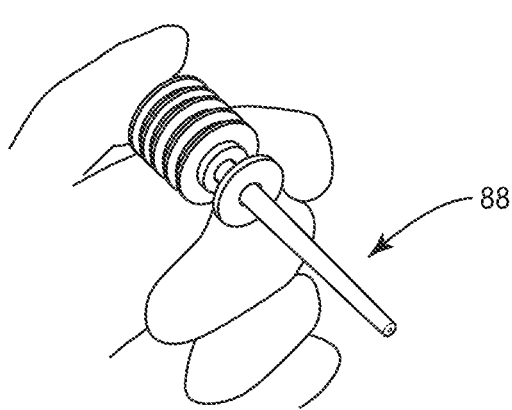
FIG. 18 is a perspective view of one embodiment of a component of the surgical system shown in FIG. 12.

Powder 86 is configured to be delivered to a surgical site via a delivery device, such as, for example, a syringe 88. In some embodiments, powder 82 is obtained by grinding an anchorage device, such as, for example, anchorage device 20 into a powder. That is, anchorage device 20 is ground into powder 82 such that powder 82 includes all of the components of anchorage device 20, including, for example, substrate 22 and coating 24. In some embodiments, powder 84 is obtained by grinding a material that includes a hemostatic agent. In some embodiments, the material is a VERISET hemostat 90 that is configured to be applied as a patch to control bleeding and is made from oxidized cellulose and a PEG compound. That is, hemostat 90 is ground into powder 84 such that powder 84 includes all of the components of hemostat 90. In some embodiments, powders 82, 84 are admixed to make powder 86. In some embodiments, powder 82 is made using a spray drying process, as shown in FIG. 16. In particular, hot air 92 acts on a slurry 94 to form particles 96 that are collected as powder 82. In some embodiments, 94 can be a slurry is made of powder 86 by mixing it with selected solvent or solvent system (THF and methanol). Powder 82 can be made from 94, which is a solution of coating polymer and drugs from device 20.

Figure 19:
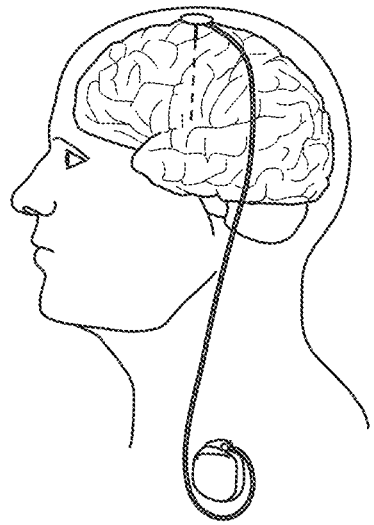
FIG. 19 is a plan view of components and anatomy used in conjunction with the surgical system shown in FIG. 12.
Figure 20:
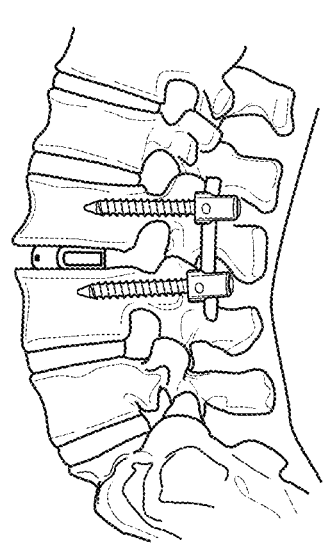
FIG. 20 is a plan view of components and anatomy used in conjunction with the surgical system shown in FIG. 12.
Figure 21:
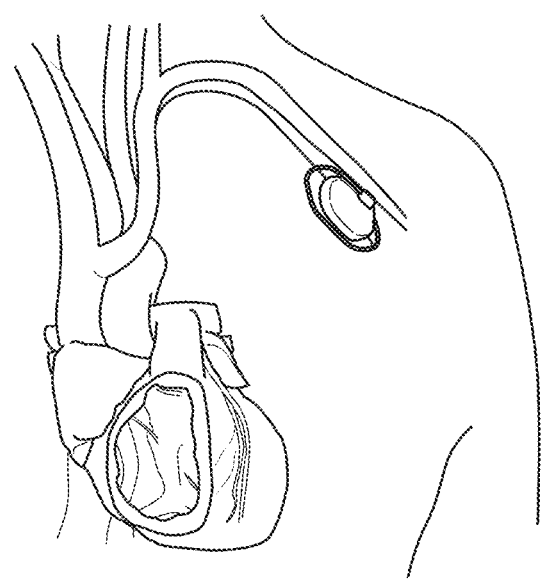
FIG. 21 is a plan view of components and anatomy used in conjunction with the surgical system shown in FIG. 12.

In some embodiments, powder 86 is administered to a surgical site to provide treatment to the surgical site via syringe 88. In some embodiments, the surgical site includes areas adjacent to the implantation of a neurostimulator, as shown in FIG. 19. In some embodiments, the surgical site includes areas adjacent to the implantation of a spinal construct, as shown in FIG. 20. In some embodiments, the surgical site includes areas adjacent to the implantation of a pacemaker, as shown in FIG. 21. In some embodiments, powder 86 is administered to the surgical site is the only treatment provided to the surgical site. In some embodiments, powder 86 is administered to the surgical site before an anchorage device, such as, for example, anchorage device 20, is coupled to a medical device present at the surgical site, such as, for example, medical device 25. In some embodiments, powder 86 is administered to the surgical site after an anchorage device, such as, for example, anchorage device 20, is coupled to a medical device present at the surgical site, such as, for example, medical device 25. In some embodiments, powder 86 is administered to the surgical site before and after an anchorage device, such as, for example, anchorage device 20, is coupled to a medical device present at the surgical site, such as, for example, medical device 25.

In some embodiments, kits are provided that include one or a plurality of anchorage devices, such as, for example, anchorage devices 20. It is contemplated that each of the anchorage devices included can have a different configuration. In some embodiments, the anchorage devices can include different coatings 24. In some embodiments, the anchorage devices can include different sizes. In some embodiments, the anchorage devices can include different shapes. In some embodiments, the anchorage devices can include different anchorage devices that are designed for use with different medical devices, such as, for example, the implantable or non-implantable medical devices discussed herein. In some embodiments, the kits include one or a plurality of medical devices, such as, for example, the implantable or non-implantable medical devices discussed herein. In some embodiments, the kit includes instructions for use. In some embodiments, the kit can include one or a plurality of powders that can be used to treat a surgical site, such as, for example, one or more powders that are the same or similar to powder 86. In some embodiments, the kit includes items that are used to make the anchorage devices, such as, for example, the materials used to make the substrate, the hemostatic agent(s), the active pharmaceutical ingredient(s), a computer with a processor capable of receiving data and communicating with a 3D printer to create an anchorage device having the parameters that were input into the computer (e.g., size, shape, material, agents/ingredients on selected areas of the substrate in selected amounts) and a 3D printer capable of making the anchorage device based upon data that is input into the computer regarding the parameters of the implant.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical device configured to surround an implantable medical device, the surgical device comprising:
    a collagen membrane; and
    a coating covering at least a portion of the membrane, the coating including an active pharmaceutical ingredient and carboxypeptidase collagen,
    wherein the membrane is free of extracellular matrix collagen.

2. The surgical device recited in claim 1, wherein the active pharmaceutical ingredient is selected from the group consisting of anesthetics, antibiotics, anti-inflammatory agents, procoagulant agents, fibrosis-inhibiting agents, anti-scarring agents, leukotriene inhibitors/antagonists, cell growth inhibitors and mixtures thereof.

3. The surgical device recited in claim 1, wherein the active pharmaceutical ingredient is a mixture of rifampin and minocycline.

4. The surgical device recited in claim 1, wherein the active pharmaceutical ingredient is selected from the group consisting of a hemostatic agent, rifampin and minocycline, and mixtures thereof.

5. The surgical device recited in claim 4, wherein the hemostatic agent is selected from a group consisting of epinephrine, tranexamic acid, chitosan and oxidized regenerated cellulose, and mixtures thereof.

6. The surgical device recited in claim 1, wherein the active pharmaceutical ingredient is selected from the group consisting of a peptide, rifampin and minocycline, and mixtures thereof.

7. The surgical device recited in claim 1, wherein the active pharmaceutical ingredient is selected from the group consisting of a pain medication, rifampin and minocycline, and mixtures thereof.

8. The surgical device recited in claim 1, wherein the membrane comprises a first piece and a second piece that is joined with the first piece, the first piece and the second piece forming a pocket having a cavity and an opening that is in communication with the cavity, the implantable medical device being configured to be inserted through the opening and into the cavity.

9. The surgical device recited in claim 1, wherein the coating comprises a polymer, the polymer comprising the active pharmaceutical ingredient.

10. The surgical device recited in claim 9, wherein the polymer is a tyrosine-derived polyarylate.

11. A surgical device configured to surround an implantable medical device, the surgical device comprising:
    a collagen membrane; and
    a coating covering at least a portion of the membrane, the coating including an active pharmaceutical ingredient,
    wherein the coating comprises carboxypeptidase collagen.

12. The surgical device recited in claim 11, wherein the active pharmaceutical ingredient is selected from the group consisting of a hemostatic agent, rifampin and minocycline, and mixtures thereof.

13. The surgical device recited in claim 12, wherein the hemostatic agent is tranexamic acid.

14. A surgical device configured to surround an implantable medical device, the surgical device comprising:
    a collagen membrane; and
    a coating covering at least a portion of the membrane, the coating including an active pharmaceutical ingredient,
    wherein the coating comprises carboxypeptidase X collagen,
    wherein the membrane comprises a first piece and a second piece that is joined with the first piece, the first piece and the second piece forming a pocket having a cavity and an opening that is in communication with the cavity, the implantable medical device being configured to be inserted through the opening and into the cavity, and
    wherein the coating comprises a polymer, the polymer comprising the active pharmaceutical ingredient.

15. The surgical device recited in claim 14, wherein the active pharmaceutical ingredient is selected from the group consisting of a hemostatic agent, rifampin and minocycline, and mixtures thereof.

16. The surgical device recited in claim 15, wherein the hemostatic agent is tranexamic acid.

* * * * *